US011081946B2

(12) United States Patent
Nagorny et al.

(10) Patent No.: US 11,081,946 B2
(45) Date of Patent: Aug. 3, 2021

(54) SWITCHED RELUCTANCE MOTOR

(71) Applicant: RESMED MOTOR TECHNOLOGIES INC., Chatsworth, CA (US)

(72) Inventors: Aleksandr S. Nagorny, Canoga Park, CA (US); Siavash Sadeghi, Northridge, CA (US); David James Fleming, Cardiff, CA (US); Michael Bruce Moir, Newbury, CA (US)

(73) Assignee: ResMed Motor Technologies Inc., Chatsworth, CA (US)

( * ) Notice: Subject to any disclaimer, the term of this patent is extended or adjusted under 35 U.S.C. 154(b) by 0 days.

(21) Appl. No.: 16/808,088

(22) Filed: Mar. 3, 2020

(65) Prior Publication Data

US 2020/0204052 A1 Jun. 25, 2020

Related U.S. Application Data

(62) Division of application No. 15/110,780, filed as application No. PCT/US2015/011703 on Jan. 16, 2015, now Pat. No. 10,742,102.

(Continued)

(51) Int. Cl.
*H02K 1/24* (2006.01)
*H02K 3/28* (2006.01)
(Continued)

(52) U.S. Cl.
CPC ....... *H02K 19/103* (2013.01); *A61M 16/0066* (2013.01); *A61M 16/0666* (2013.01);
(Continued)

(58) Field of Classification Search
CPC ........ H02K 19/103; H02K 3/28; H02K 1/246; H02K 1/24; H02K 11/22; H02K 5/04;
(Continued)

(56) References Cited

U.S. PATENT DOCUMENTS

| 4,940,912 A | 7/1990 | Kant et al. |
| 5,111,095 A | 5/1992 | Hendershot |

(Continued)

FOREIGN PATENT DOCUMENTS

| CN | 1038728 A | 1/1990 |
| CN | 102035333 A | 4/2011 |

(Continued)

OTHER PUBLICATIONS

Chinese Search Report for CN201580004872.8 dated Feb. 12, 2018.
(Continued)

*Primary Examiner* — Thomas Truong
(74) *Attorney, Agent, or Firm* — Botos Churchill IP Law LLP

(57) ABSTRACT

A stator assembly has coils in a distributed winding configuration. A poly-phase switched reluctance motor assembly 3002 may include a stator assembly with multiple coils in a distributed winding configuration. The stator assembly may have a central bore into which a rotor assembly having multiple poles is received and configured to rotate. A method of controlling a switched reluctance motor may include at least three phases wherein during each conduction period a first phase is energized with negative direction current, a second phase is energized with positive current and there is at least one non-energized phase. During each commutation period either the first phase or second phase switches off to a non-energized state and one of the non-energized phases switches on to an energized state with the same direction current as the first or second phase that was switched off. The switched reluctance motor may include a distributed winding configuration.

17 Claims, 27 Drawing Sheets

Related U.S. Application Data

(60) Provisional application No. 61/928,547, filed on Jan. 17, 2014.

(51) Int. Cl.

| | | |
|---|---|---|
| *A61M 16/00* | (2006.01) | |
| *H02K 19/10* | (2006.01) | |
| *H02K 5/04* | (2006.01) | |
| *H02K 11/22* | (2016.01) | |
| *A61M 16/10* | (2006.01) | |
| *H02P 25/098* | (2016.01) | |
| *A61M 16/06* | (2006.01) | |
| *A61M 16/08* | (2006.01) | |
| *A61M 16/16* | (2006.01) | |

(52) U.S. Cl.
CPC ...... *A61M 16/0875* (2013.01); *A61M 16/109* (2014.02); *A61M 16/1095* (2014.02); *A61M 16/16* (2013.01); *H02K 1/246* (2013.01); *H02K 3/28* (2013.01); *H02K 5/04* (2013.01); *H02K 11/22* (2016.01); *H02P 25/098* (2016.02); *A61M 2202/0208* (2013.01); *A61M 2205/18* (2013.01); *A61M 2205/3331* (2013.01); *A61M 2205/42* (2013.01); *A61M 2205/502* (2013.01); *A61M 2205/75* (2013.01); *A61M 2230/40* (2013.01)

(58) Field of Classification Search
CPC ............ A61M 16/109; A61M 16/1095; A61M 16/0066; A61M 16/0666; A61M 16/0875; A61M 16/16; A61M 2202/0208; A61M 2205/18; A61M 2205/3331; A61M 2205/42; A61M 2205/502; A61M 2205/75; A61M 2230/40; H02P 25/098
USPC ................... 310/179, 180, 216.075
See application file for complete search history.

(56) References Cited

U.S. PATENT DOCUMENTS

| | | | |
|---|---|---|---|
| 5,239,217 A | 8/1993 | Horst | |
| 5,719,453 A | 2/1998 | Horst | |
| 5,804,896 A * | 9/1998 | Takehara | H02K 1/165 310/179 |
| 5,811,905 A | 9/1998 | Tang | |
| 6,028,385 A | 2/2000 | Pengov et al. | |
| 6,194,804 B1 * | 2/2001 | Nashiki | H02K 1/246 310/166 |
| 6,246,193 B1 * | 6/2001 | Dister | H02P 6/185 318/254.2 |
| 2004/0222779 A1 | 11/2004 | Cock et al. | |
| 2006/0001394 A1 * | 1/2006 | Yukumatsu | B62D 5/046 318/632 |
| 2008/0072900 A1 * | 3/2008 | Kenyon | A61M 16/16 128/204.18 |
| 2009/0087299 A1 | 4/2009 | Agrawal et al. | |
| 2010/0123426 A1 | 5/2010 | Nashiki | |
| 2012/0086288 A1 | 4/2012 | Tanaka et al. | |
| 2013/0076212 A1 | 3/2013 | Park et al. | |
| 2013/0259674 A1 | 10/2013 | Sears et al. | |
| 2014/0231116 A1 * | 8/2014 | Pollock | B25B 23/147 173/183 |

FOREIGN PATENT DOCUMENTS

| | | |
|---|---|---|
| CN | 102083492 A | 6/2011 |
| CN | 102447320 A | 5/2012 |
| GB | 2491194 A | 11/2012 |
| JP | H05308795 A | 11/1993 |
| JP | H0746809 | 2/1995 |
| WO | 0113508 A1 | 2/2001 |
| WO | 200915621 A1 | 2/2009 |

OTHER PUBLICATIONS

Extended European Search Report for Application No. EP15737859 dated Aug. 16, 2017.
International Search Report and Written Opinion for Application No. PCT/US15/11703 dated Apr. 17, 2015.

* cited by examiner

SWITCHED RELUCTANCE MOTOR

1 CROSS-REFERENCE TO RELATED APPLICATIONS

This application is a divisional of U.S. patent application Ser. No. 15/110,780, filed Jul. 11, 2016, which is a national phase entry of International Application No. PCT/US2015/011703, filed Jan. 16, 2015, published in English, and which claims priority from U.S. Provisional Patent Application No. 61/928,547, filed on Jan. 17, 2014, the disclosure of all of which are hereby incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE INVENTION

5.1 Field of the Invention

The present technology relates to electronically commutated motors, particularly switched reluctance motors, and the use thereof. These types of electronically commutated motors produce continuous rotational torque without the use of permanent magnets. The present technology further relates to switched reluctance motors having a small size and low noise output. In some aspects the motors may be used in medical devices or apparatus configured to treat, prevent and/or ameliorate respiratory-related disorders.

5.2 Description of the Related Art

5.2.1 Electronically Commutated Motors

One of the subgroups of electronically commutated motors are brushless D.C. motors. Brushless D.C. motors are well known and used in a range of devices. Brushless D.C. motors typically include permanent magnets coupled to or on a rotor and windings formed on a laminated stator that form electromagnets when current is applied to the stator. High energy permanent magnets used in motors may be made from materials which include rare earth metals such as samarium-cobalt and neodymium-iron-boron. However, such permanent magnets are expensive resulting in a higher cost motor. Furthermore the availability of these rare earth metals is limited. To reduce costs other forms of brushless D.C. motors that do not require permanent magnets or windings associated with the rotor were developed.

Another class of electronically commutated motors that do not include permanent magnets are called switched reluctance (SR) motors. Switched reluctance motors run by creating reluctance torque, which is proportional to the difference of aligned and non-aligned values of the self-inductance in the SR motor. Conventional SR motors comprise concentrated windings in the stator that produce torque due to the self-inductance variation slope of one phase and the positive DC current applied to that phase. The inductance ratio between the aligned inductance and the unaligned inductance is important in generating torque and may vary in the range of 3-8. Consequently SR motors are used for the applications where the input power level exceeds several hundred watts and are generally larger motors with stator outer diameters greater than 50 mm. Such prior art SR motors have been used to drive devices such as automotives, vacuum cleaners and washing machines and other large applications. They have not been suitable for driving low power (less than a hundred watts) or small (stator outer diameters less than 50 mm) high speed devices (up to 60,000 rpm) due to the failure to produce enough torque in a small arrangement having low inductance ratios. SR motors have also been used in conditions where severe environmental conditions occur such as in high or low temperatures.

The stators of SR motors are generally wound with three, four or five phases in a concentrated winding arrangement. Typically a SR motor has less rotor poles than stator poles. FIG. 1 shows an example of a three phase SR motor stator and rotor arrangement. The three phases are made up of three groups of concentrated windings: 10a, 10b, 10c, and 10d form a first phase; 12a, 12b, 12c and 12d form a second phase; and 14a, 14b, 14c and 14d form the third phase. In such a concentrated arrangement a coil with sides 10a and 10b, is wound around a stator tooth or pole 22 of the stator 20, thus the windings are concentrated around one stator tooth 22. The rotor 30 is formed of a soft magnetic material, for example laminated silicon steel, and includes salient magnetic poles 32 to create a difference in magnetic reluctance between rotor and stator along the poles and between the poles.

Generally SR motors have been driven by applying current to energize a single stator phase at one time and switching the current between stator phases to cause rotation of the rotor. A flux is generated through the energized stator poles and the rotor poles, which pulls the rotor poles towards and into alignment with the energized stator poles. Switching the current to a second adjacent stator phase results in the pulling of the rotor poles to align with the second stator phase. The continuous switching of the current in a sequence to adjacent stator phases around the stator results in rotation of the rotor. Controlling the timing of the current switching controls the continuity of the rotor rotation. Switching the current at the optimum position of the rotor is desired to reduce torque ripple or cogging as the rotor rotates. Torque ripple may result in vibration and noise within the motor. In attempts to reduce torque ripple the current being applied to adjacent phases during the switching step has been overlapped. However, when current is applied to two phases of a conventional SR motor in synchronism the motor is less efficient, as there is no significant increase in torque despite twice the power input being provided.

In such SR motors one rotor pole is generally configured to align with a single stator pole when the rotor is pulled into alignment with the energized stator pole. For example as seen in FIG. 1, when stator phase 10, including stator coil sides 10a & 10b and 10c & 10d have been energized the rotor poles, 32b and 32c are pulled to align with stator teeth 1 and 4 respectively. Consequently the normal or radial components of the electromagnetic forces are applied to stator teeth and rotor poles. Such radial forces may be relatively high and can be a source of vibration and noise within the motor.

Some efforts have been made to reduce the motor noise produced by SR motors. For example U.S. Pat. No. 5,239,217 describes a multiple phase SR motor comprising a stator with concentrated windings and multiple rotor poles. Each of the stator poles and the rotor poles may comprise multiple teeth. The stator includes at least one redundant pole set for each motor phase to help distribute ovalising forces on the motor assembly as it rotates and reduce motor noise. U.S. Pat. No. 6,028,385 suggests reducing the torque ripple effect by using rotor poles having 2 wide rotor poles and 2 narrow rotor poles. The three phase reluctance motor has concentrated windings and includes 12 stator poles with the 4 rotor poles. During each energization phase, where one phase is energized at a time the rotor is sequentially advanced such that the leading edge of a wide rotor pole interacts with a first energized stator pole and then a narrow rotor pole is drawn into alignment with a second energized stator pole of the same phase. However, to enable significant torque to be produced from such arrangements these SR motors would be required to be relatively large to maintain an inductance ratio of approximately 7 with the increased number of stator poles.

U.S. Pat. No. 5,111,095 is said to provide a SR motor producing increased torque and efficiency. The SR motor comprises a stator having evenly spaced concentrated winding poles and a rotor with unevenly spaced rotor poles. Two adjacent phases are energized at all times in order to provide controlled rotation of the rotor. The adjacent windings are coiled in a direction about the poles of the stator in a manner that causes the polarity of the stator poles to have opposite polarities when the pair is energized with a current so as to create a magnetic circuit between the poles of each pair. The pairs of adjacent stator poles align with half (e.g. 4) of the rotor poles and when the next pair of adjacent stator poles are energized these align with the other half (e.g. further 4) of the rotor poles. Such a SR motor arrangement would not be suitable for use in high speed small devices.

Chinese Patent Publication no. CN 102035333A is said to describe a permanent magnet switched reluctance motor adopting a distributed winding. The stator adopts a three-phase armature winding with a distributed structure, only one winding coil is arranged between adjacent stator tooth slot bodies, coils which pass over two stator slots are connected together to form a winding of one phase. A permanent magnet is also embedded into the stator. The ratio of the number of the stator teeth to the number of the rotor teeth is 6:4, and the number of their poles is in the form of 6/4 or 12/8.

There is further need to reduce one or more of the noise, vibration and/or size of SR motors if they are to be used in medical devices and/or conditions where low noise is important, such as during sleep.

5.2.2 Motor Applications

Motors are used to drive a variety of devices in a diverse range of applications including but not limited to fans, pumps, medical devices, automotive industry, aerospace, toys, power tools, disk drives, and household appliances. Motors have been used in medical devices to generate a supply of pressurized gas for example in Positive Airway Pressure (PAP) devices and ventilators. These devices generally include permanent magnet brushless D.C. motors. SR motors generally have not been used in such devices due to the generally larger size and higher level of noise of SR motors.

The noise produced by some medical devices is required to be relatively low so as not to disturb the user. In particular for medical devices that may be used for long periods of time, such as throughout the day, and/or during sleep, such as PAP devices and/or ventilators the level of noise emitted is a significant issue. Sound pressure values of a variety of objects are listed below:

| Object | A-weighted sound pressure dB(A) | Notes |
| --- | --- | --- |
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| ResMed S9 AutoSet ™ PAP device | 26.5 | |
| Background in TV studio | 20 | |

6 BRIEF SUMMARY OF THE TECHNOLOGY

The present technology is directed towards switched reluctance motors and devices that comprise such switched reluctance motors.

A first aspect of the present technology relates to switched reluctance motor comprising a stator having a distributed winding configuration.

Another aspect of the present technology relates to switched reluctance motor having higher total torque and distributed force.

Another aspect of the present technology relates to switched reluctance motor having reduced radial forces and noise output.

Another aspect of the present technology relates to a switched reluctance motor with a stator having an inductance ratio of less than 3. For example, technology relates to a switched reluctance motor with a stator having an aligned-to-unaligned inductance ratio of less than 3.

One form of the present technology comprises a poly-phase switched reluctance motor assembly comprising a stator assembly including a plurality of coils and a stator with a central bore, and a rotor assembly having a plurality of poles. The rotor assembly is arranged within the central bore of the stator assembly and configured to rotate therein and the plurality of coils is configured in a distributed winding configuration.

Furthermore, the stator of the poly-phase switched reluctance motor assembly may include a plurality of projecting stator teeth forming a plurality of stator slots therebetween. Each of the plurality of stator slots may comprise one of the plurality of coils. The total number of stator slots may be determined as a function of a number of phases and a number of rotor poles of the motor. The determination of the total number of stator slots may further include a winding distribution parameter.

In some aspects the plurality of coils may include a coil group for each phase of the poly-phase switched reluctance motor and each of the coils for each coil group are uniformly distributed between the stator slots. Each coil group comprises at least one coil.

In some aspects the poly-phase switched reluctance motor assembly may include at least three motor phases and in use two motor phases are energized at one time during a conduction period. Furthermore one of the two energized phases is provided with a positive direction current and the second of the two energized phases is provided with a negative direction current. Additionally one of the two energized phases may be switched off to a non-energized state and one of the non-energized phases may be switched on to an energized state during each commutation period.

Some aspects of the present technology include a poly-phase switched reluctance motor assembly wherein in use each phase of the motor is energized with the same current value during at least two consecutive conduction periods.

One form of the present technology comprises a poly-phase switched reluctance motor assembly including a stator having an outer diameter less than 50 mm.

Another aspect of one form of the present technology is a stator for a poly-phase switched reluctance motor comprising a plurality of stator teeth separated by stator slots and surrounding a central bore and a plurality of coils that are configured in a distributed winding configuration. The plurality of coils may include a coil group for each phase of the poly-phased switched reluctance motor and the coil group may include one or more coils. The central bore of the stator assembly is configured to receive a rotor assembly having a plurality of poles. Furthermore each of the stator slots may comprise one of the plurality of coils.

Another aspect of one form of the present technology is a stator for a poly-phase switched reluctance motor having an inductance ratio of less than 3.

Another aspect of one form of the present technology is a stator for a poly-phase switched reluctance motor having an outer diameter of less than 50 mm.

Another aspect of one form of the present technology is a positive airway pressure device comprising a poly-phase switched reluctance motor including a stator having a distributed winding configuration. The positive airway pressure device configured to provide a supply of pressurized breathable gas.

Another aspect of one form of the present technology is a system for treating a respiratory disorder comprising a therapy device configured to provide a supply of pressurized breathable gas, the therapy device comprising a poly-phase switched reluctance motor including a stator having a distributed winding configuration. The system may further include an air delivery conduit and a patient interface configured to receive the supply of pressurized gas from the therapy device via the air delivery conduit and deliver the supply of pressurized gas to a patient. The system may additionally include a humidifier configured to humidify the supply of pressurized gas.

An aspect of one form of the present technology is a method of controlling a switched reluctance motor comprising at least three phases. The method comprising during each conduction period energizing a first phase with a negative direction current, energizing a second phase with a positive current and having at least one non-energized phase and during each commutation period switching off one of the first phase or the second phase to a non-energized state and switching on one of the non-energized phases to an energized state with the same direction current as the first or second phase that was switched off. Furthermore the switched reluctance motor may include a distributed winding configuration.

Embodiments of the switched reluctance motor may be implemented without the use of permanent magnets for rotation of the rotor or such as having no permanent magnets within the stator.

Of course, portions of the aspects may form sub-aspects of the present technology. Also, various ones of the sub-aspects and/or aspects may be combined in various manners and also constitute additional aspects or sub-aspects of the present technology.

Although described in relation to medical devices the SR motors of the present technology may be used in a range of applications.

Other features of the technology will be apparent from consideration of the information contained in the following detailed description, abstract, drawings and claims.

7 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

7.1 Motor

7.2 Motor Assembly

Figure 3A:
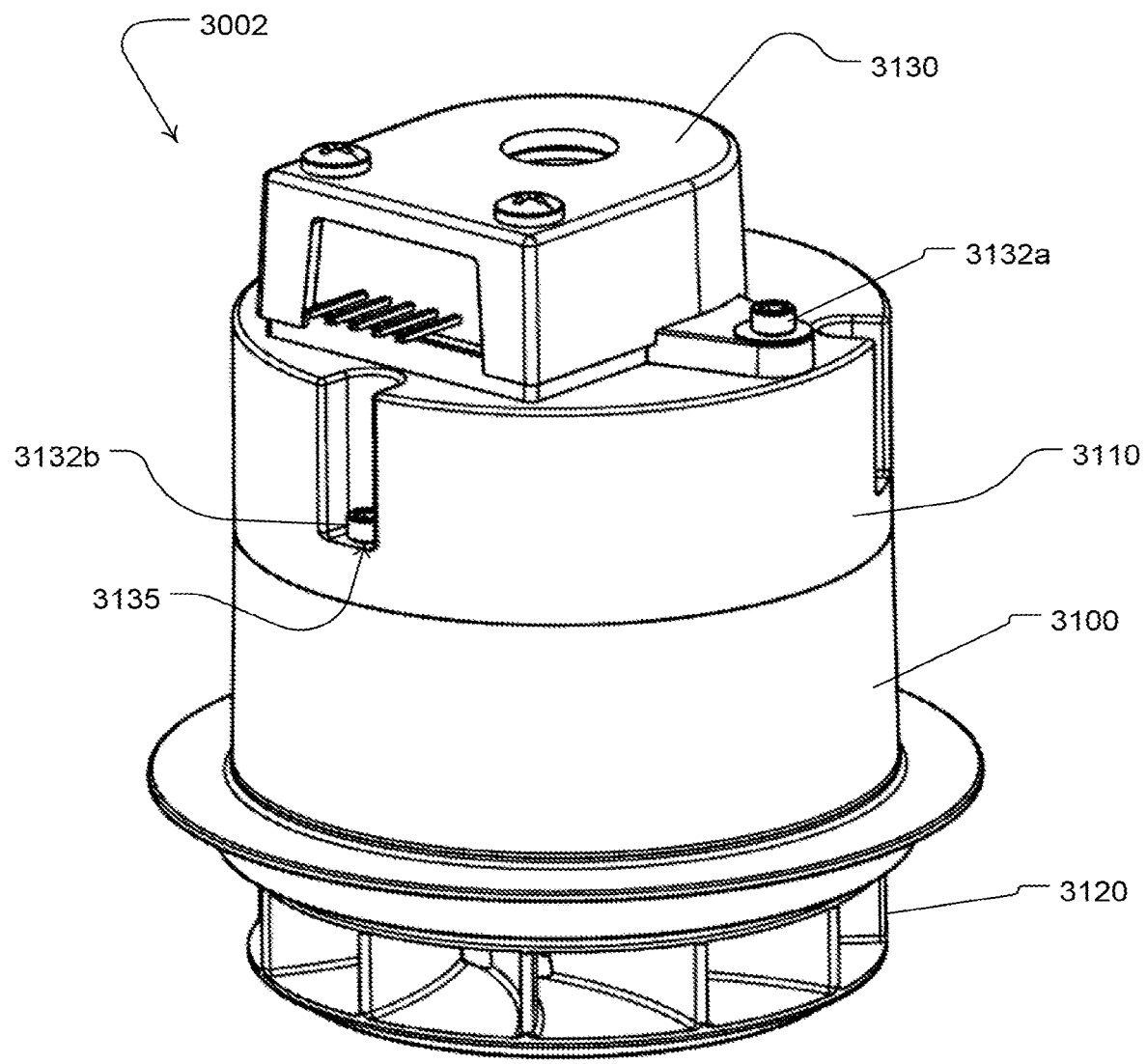

FIG. 3A is a perspective view of an example motor assembly in some implementations of the present technology.

Figure 3B:
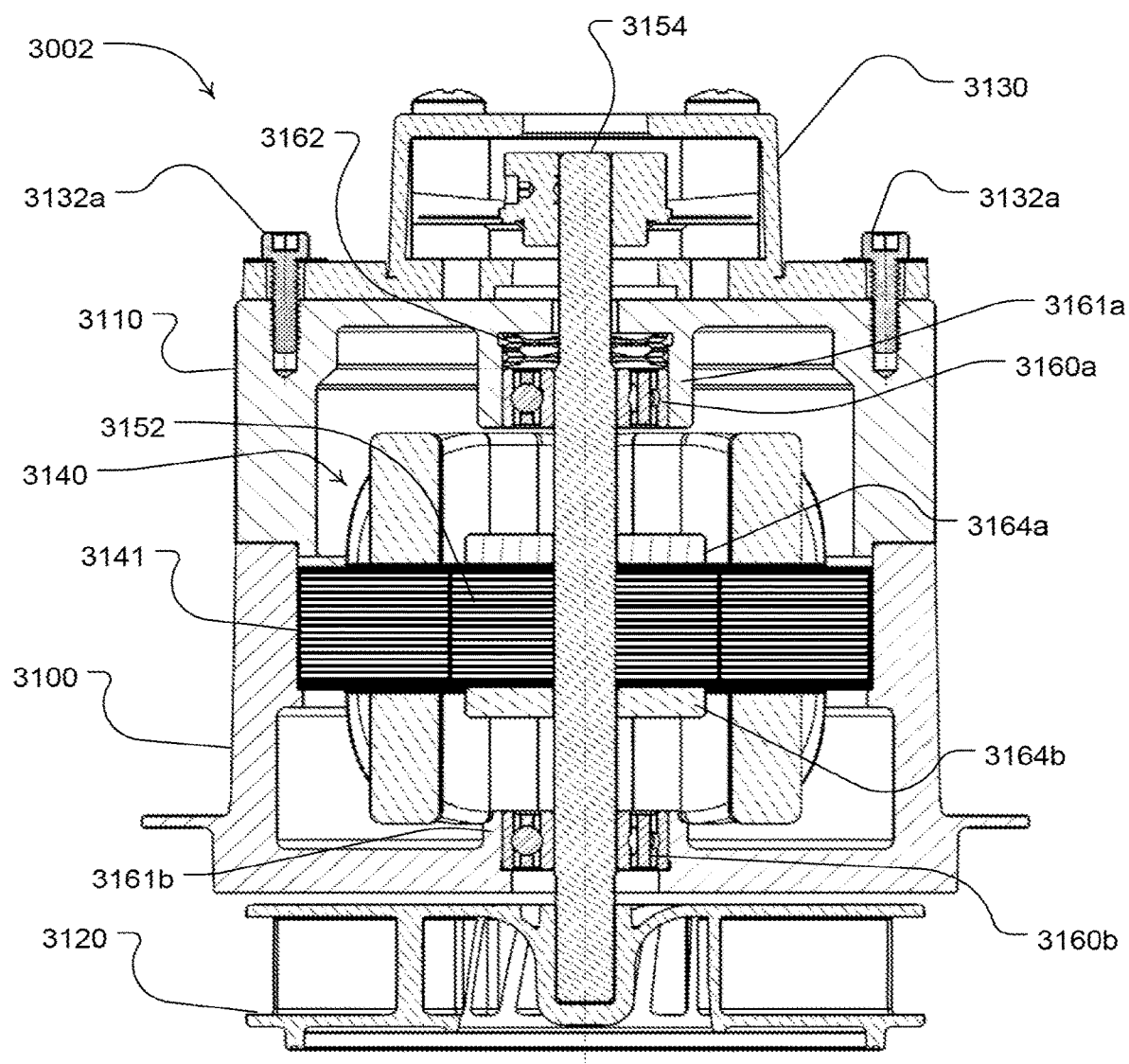

FIG. 3B is a cross sectional view of the motor assembly of FIG. 3A.

Figure 3C:
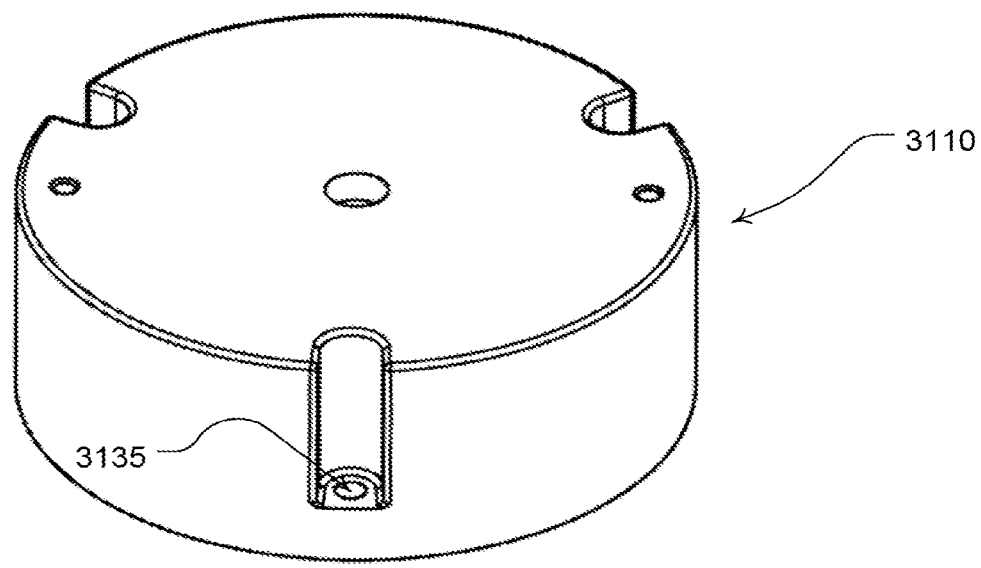
Figure 3D:
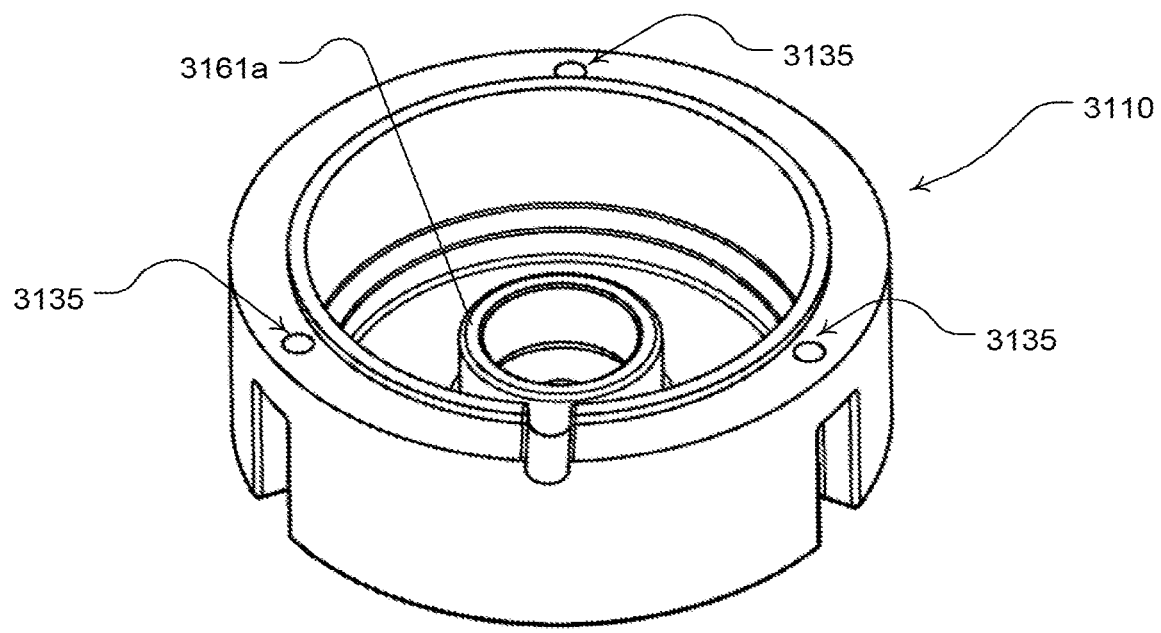

FIGS. 3C and 3D show outside and inside perspective views respectively of an end bell housing component of the motor assembly of FIG. 3A.

Figure 3E:
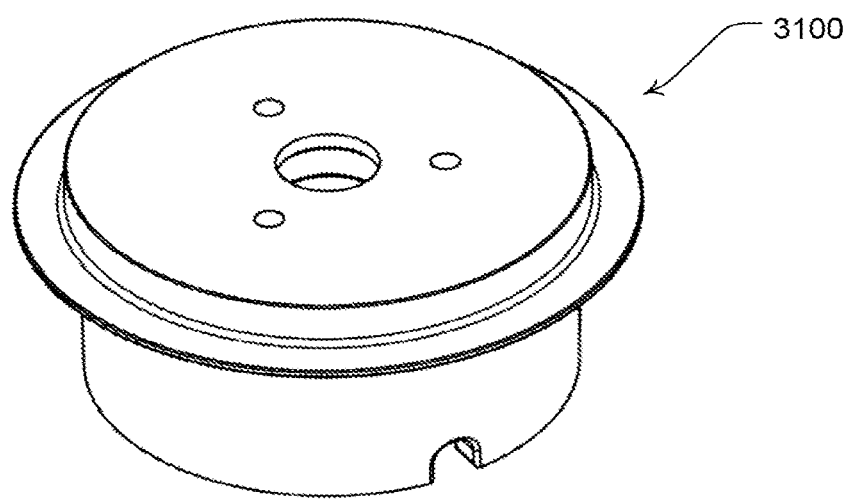
Figure 3F:
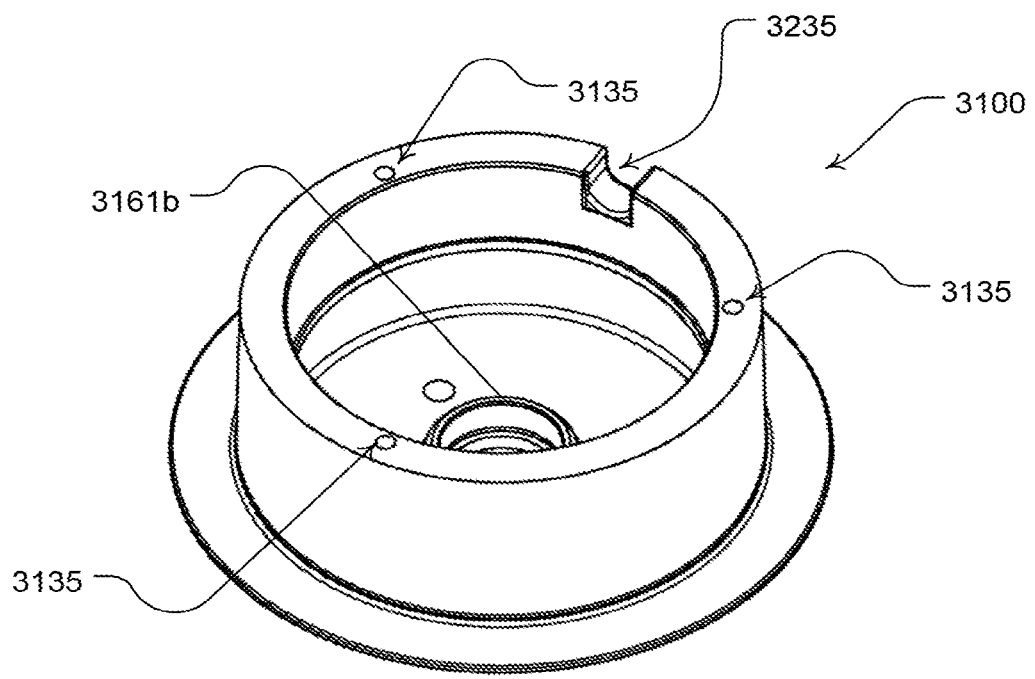

FIGS. 3E and 3F show outside and inside perspective views respectively of a housing of the motor assembly of FIG. 3A.

Figure 3G:
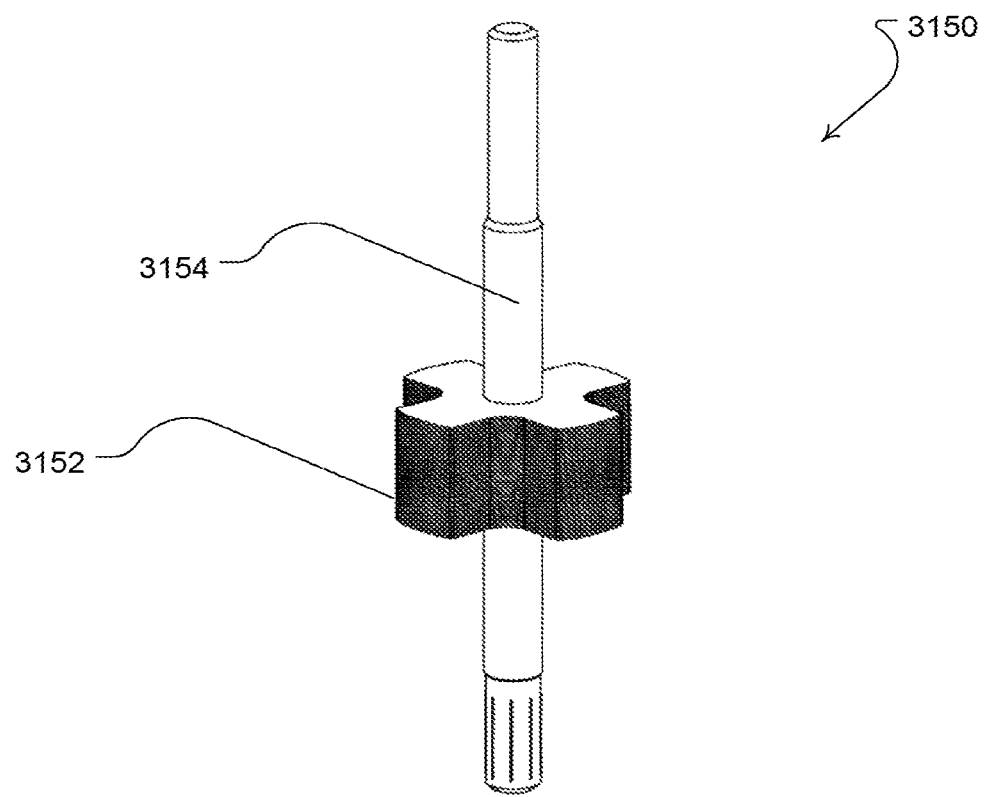

FIG. 3G is an perspective view of an example rotor assembly for the motor assembly of FIG. 3A.

Figure 3H:
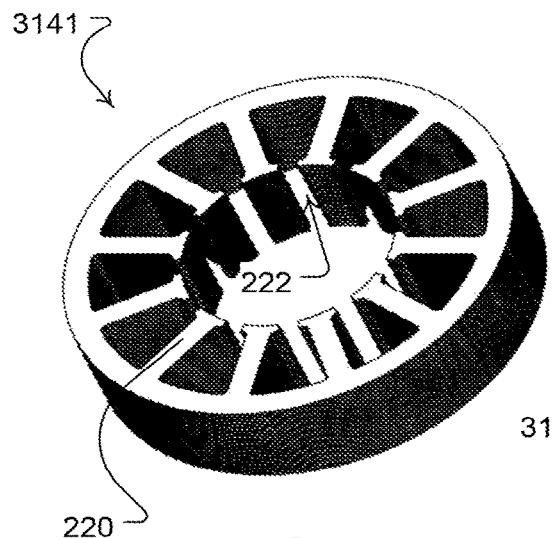

FIG. 3H is a perspective view of an example stator suitable for implementation in the motor assembly of FIG. 3A.

Figure 3J:
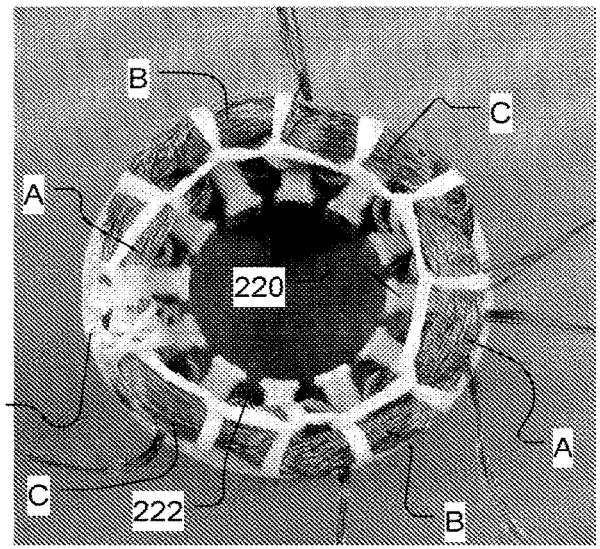
Figure 3I:
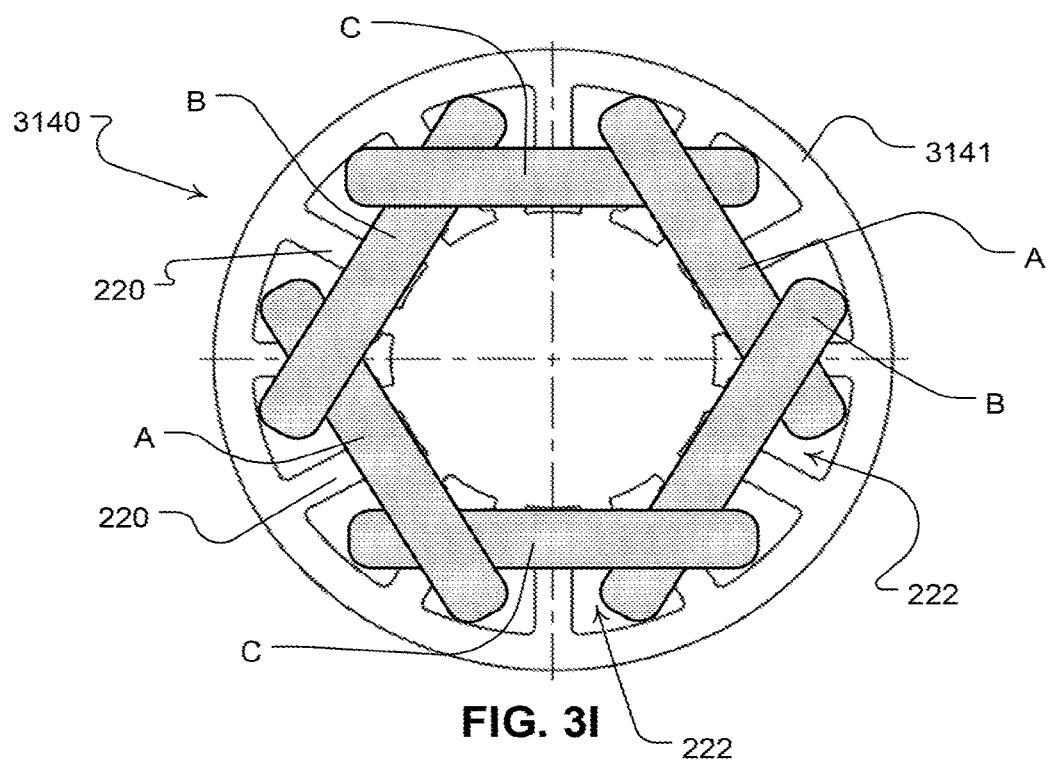

FIG. 3I is a schematic plan view of the stator assembly of FIG. 3H illustrating inclusion of phase coils.

FIG. 3J is a top view illustration of a wound stator.

7.3 System

Figure 4:
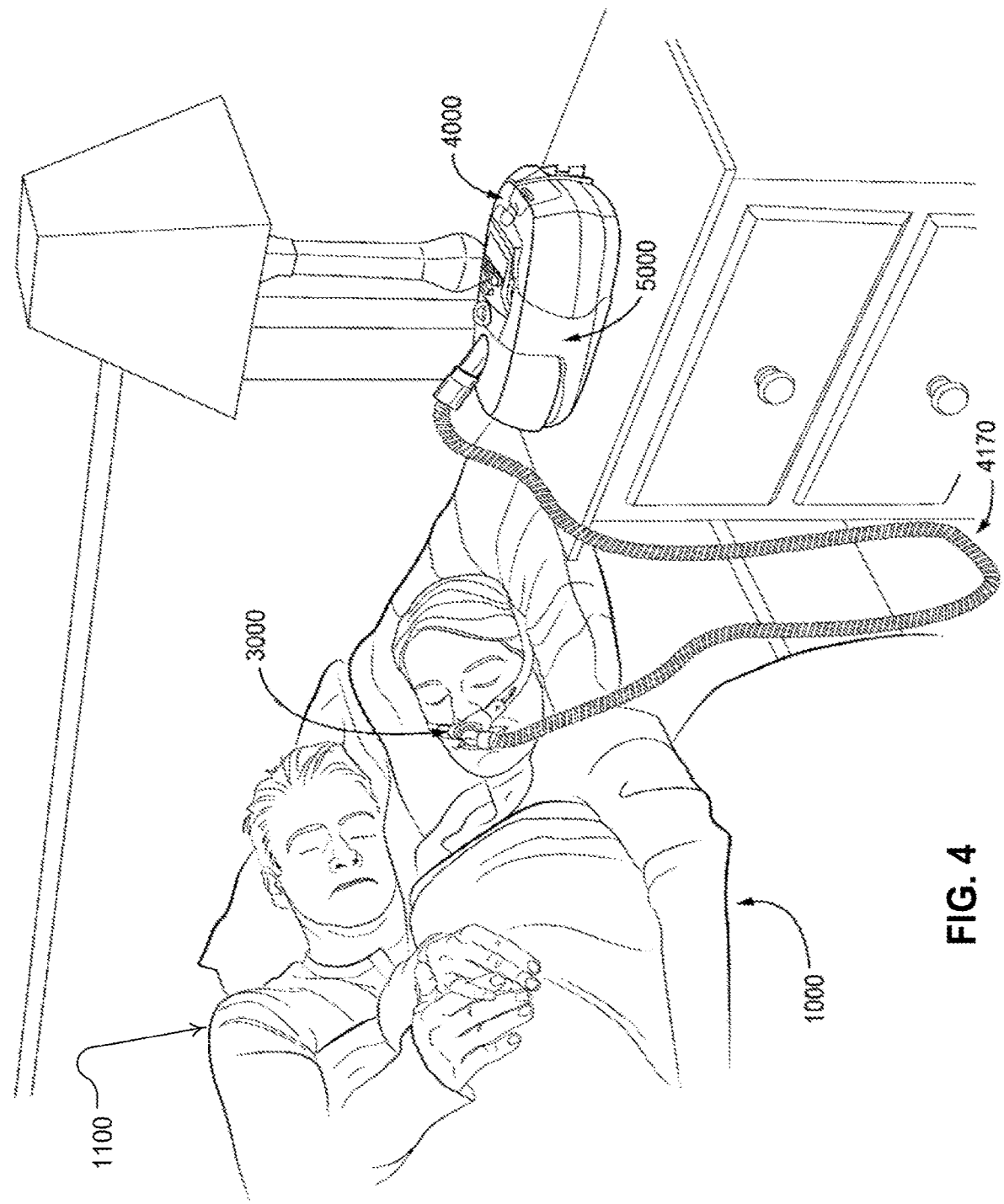

FIG. 4 shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000. A bed partner 1100 may also be present when the patient uses the system.

7.4 Pap Device

Figure 5A:
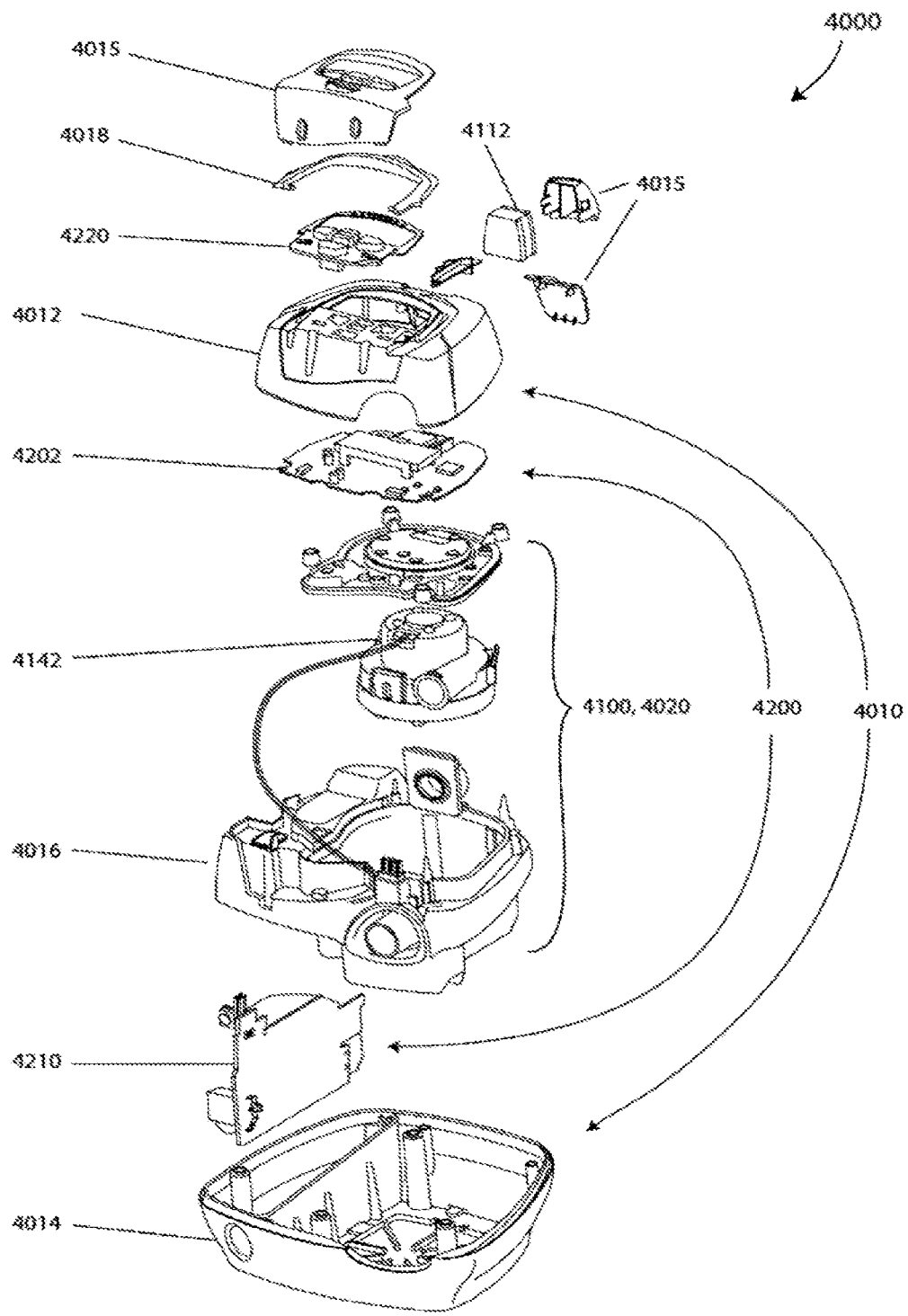

FIG. 5A shows a PAP device in accordance with one form of the present technology.

Figure 5B:
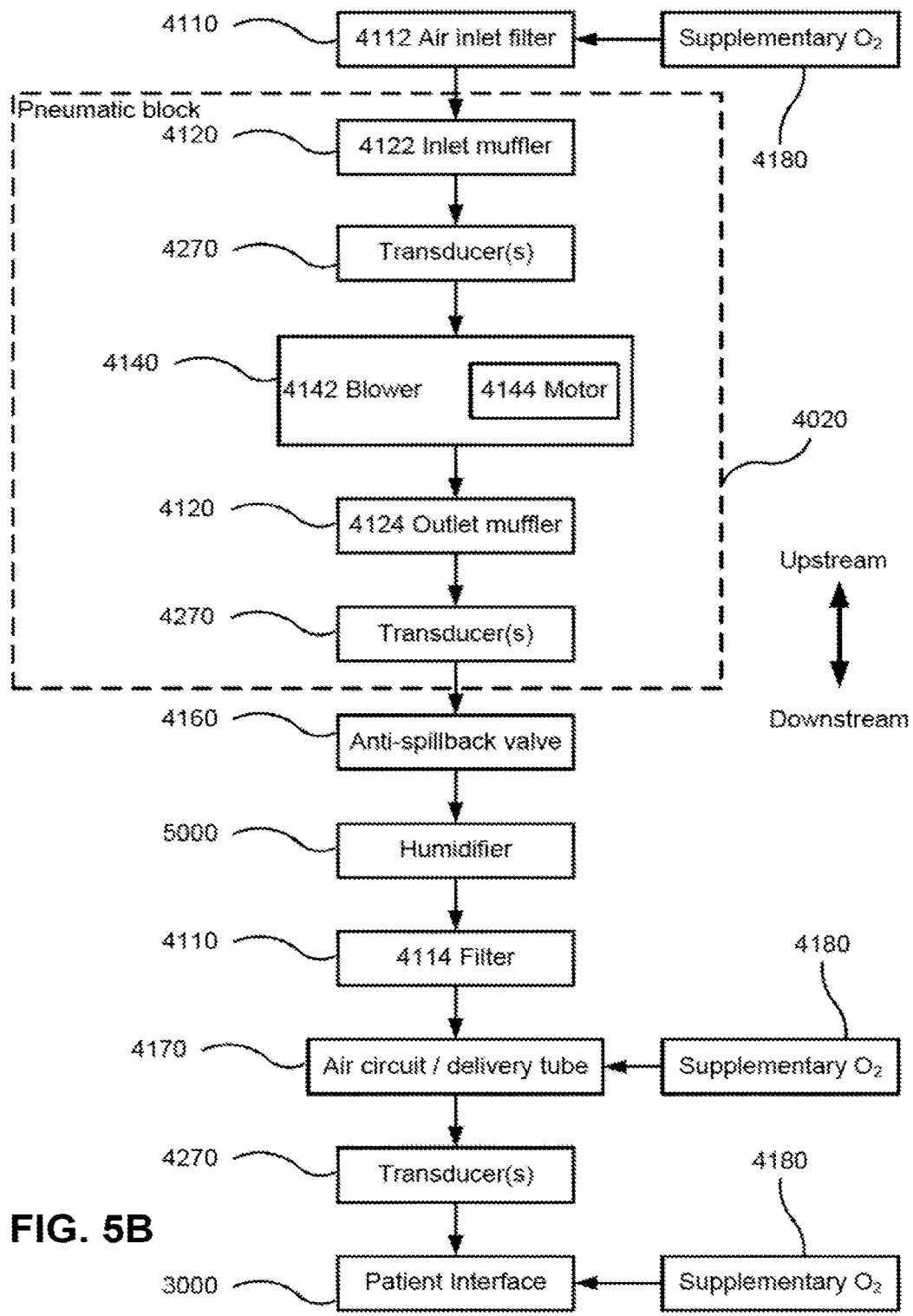

FIG. 5B shows a schematic diagram of the pneumatic circuit of a PAP device in accordance with one form of the present technology. The directions of upstream and downstream are indicated.

Figure 5C:
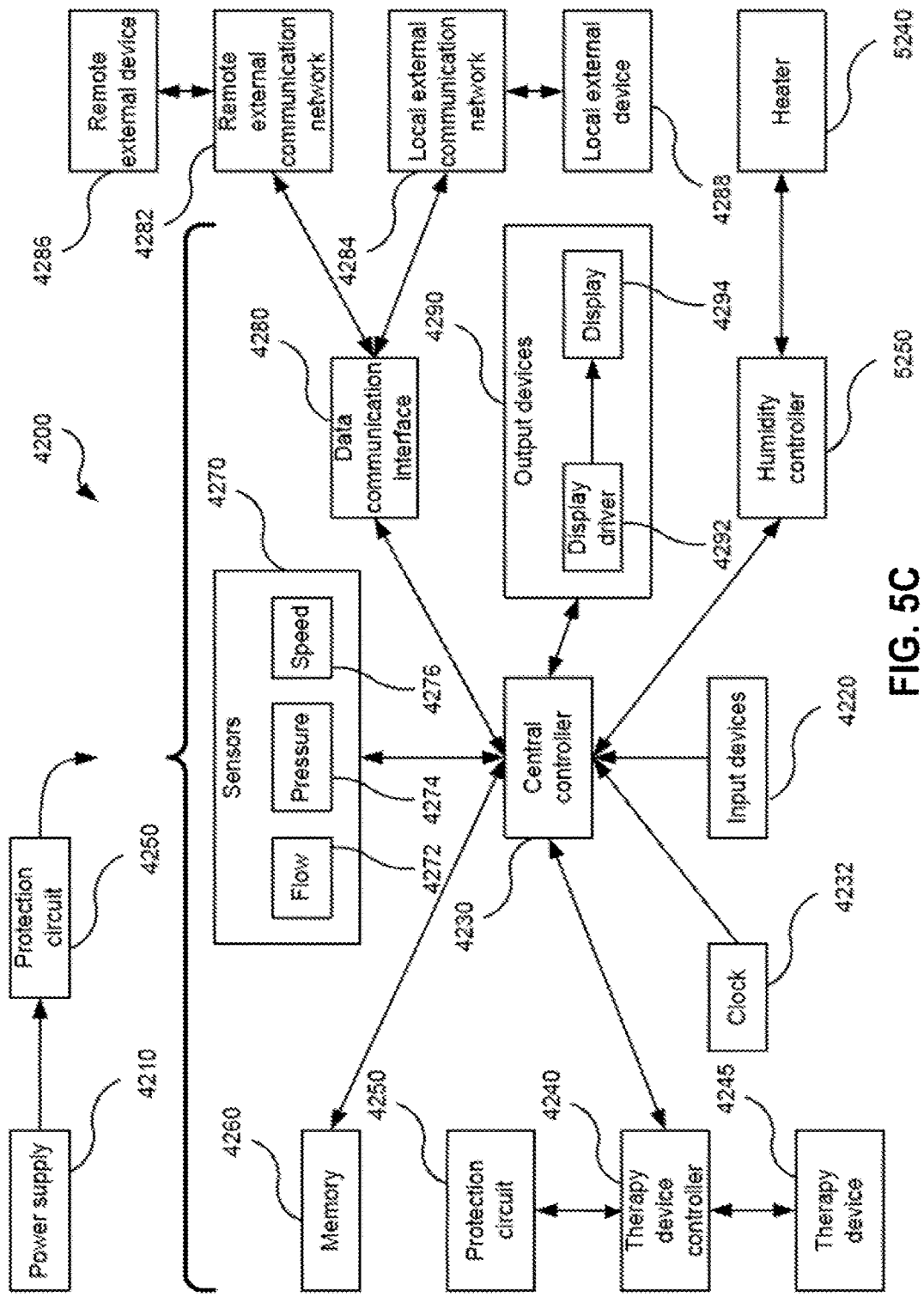

FIG. 5C shows a schematic diagram of the electrical components of a PAP device in accordance with one aspect of the present technology.

Figure 5D:
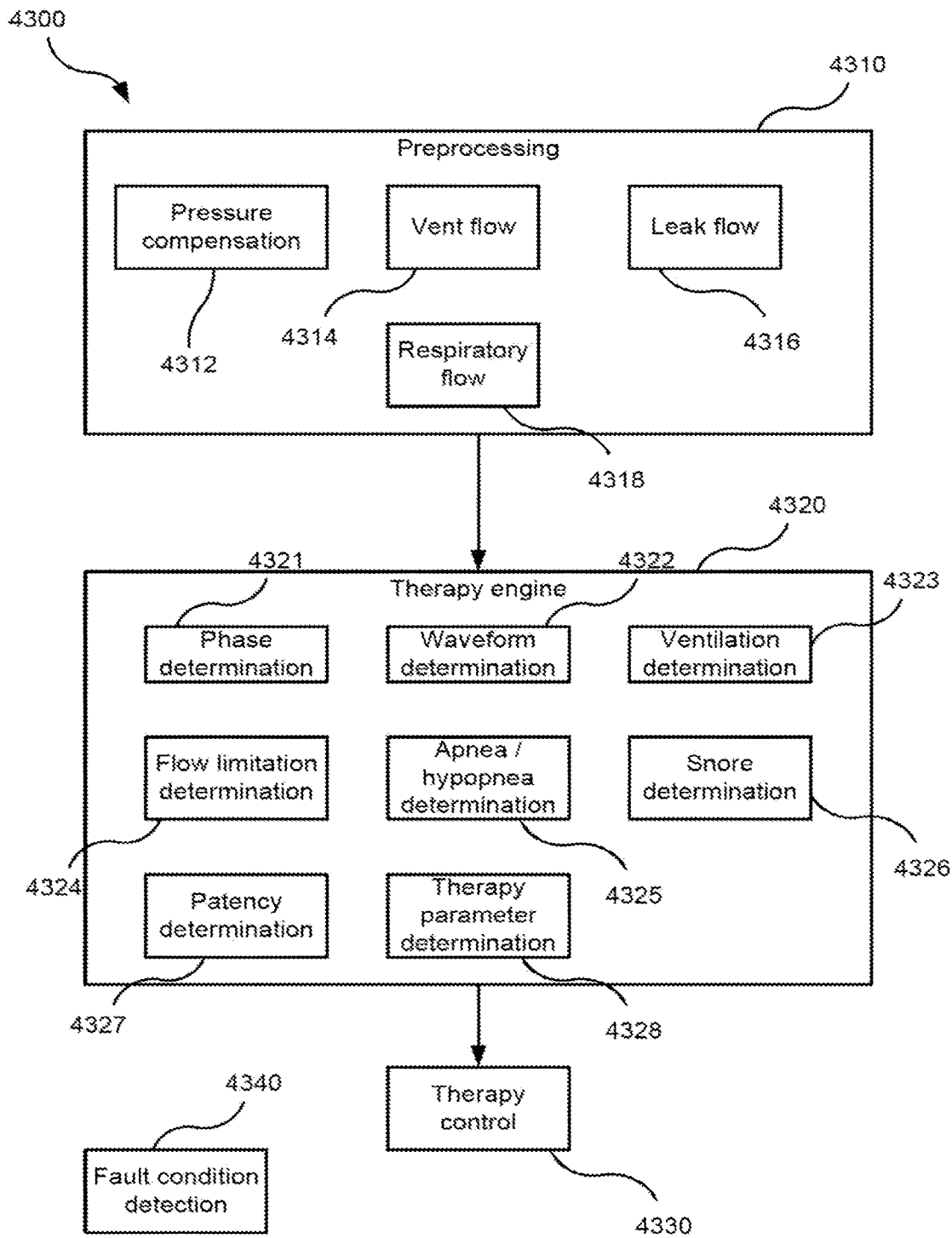

FIG. 5D shows a schematic diagram of the algorithms implemented in a PAP device in accordance with an aspect of the present technology. In this figure, arrows with solid lines indicate an actual flow of information, for example via an electronic signal.

Figure 5E:
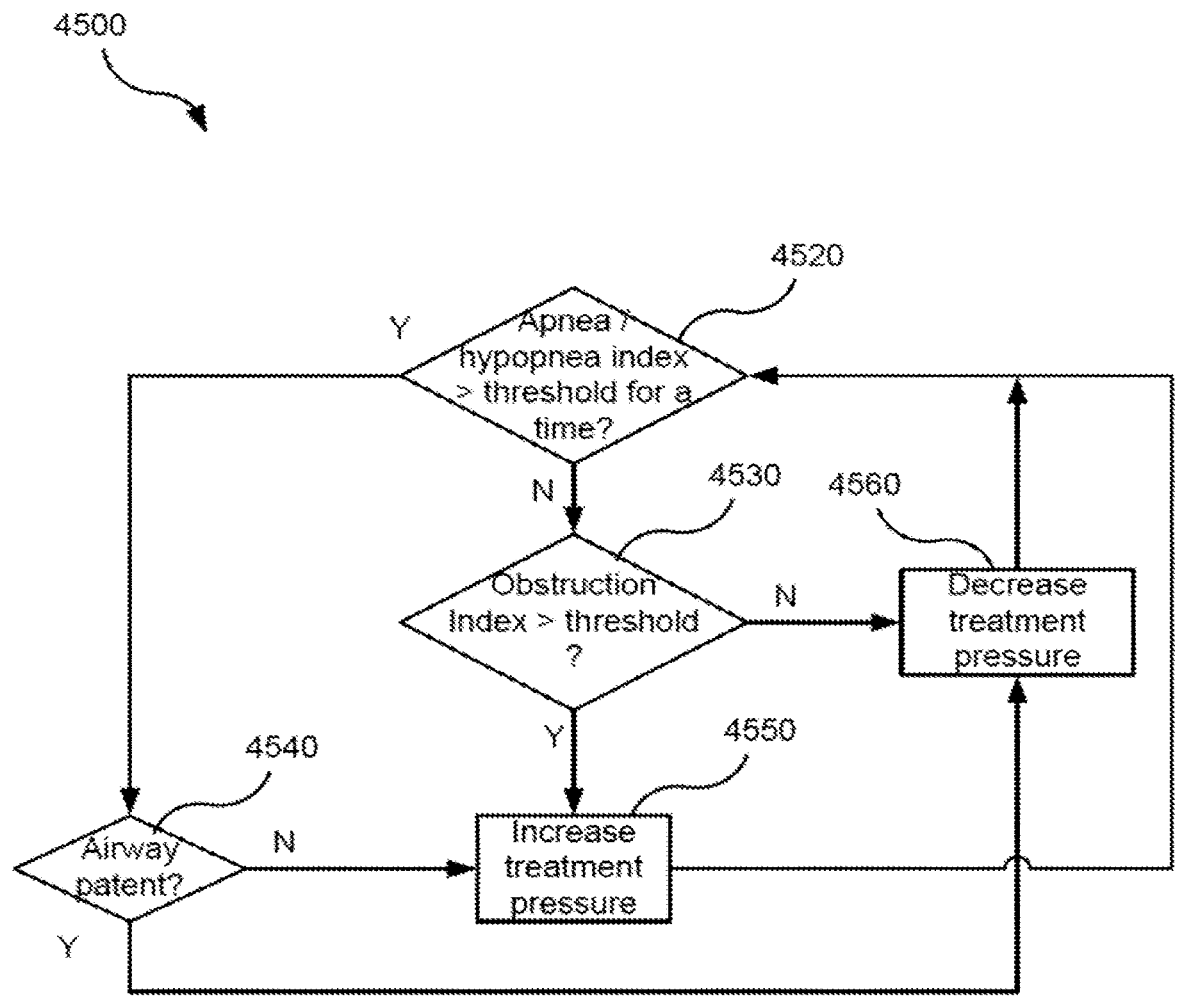

FIG. 5E is a flow chart illustrating a method carried out by the therapy engine module of FIG. 5D in accordance with one form of the present technology.

7.5 Humidifier

Figure 6A:
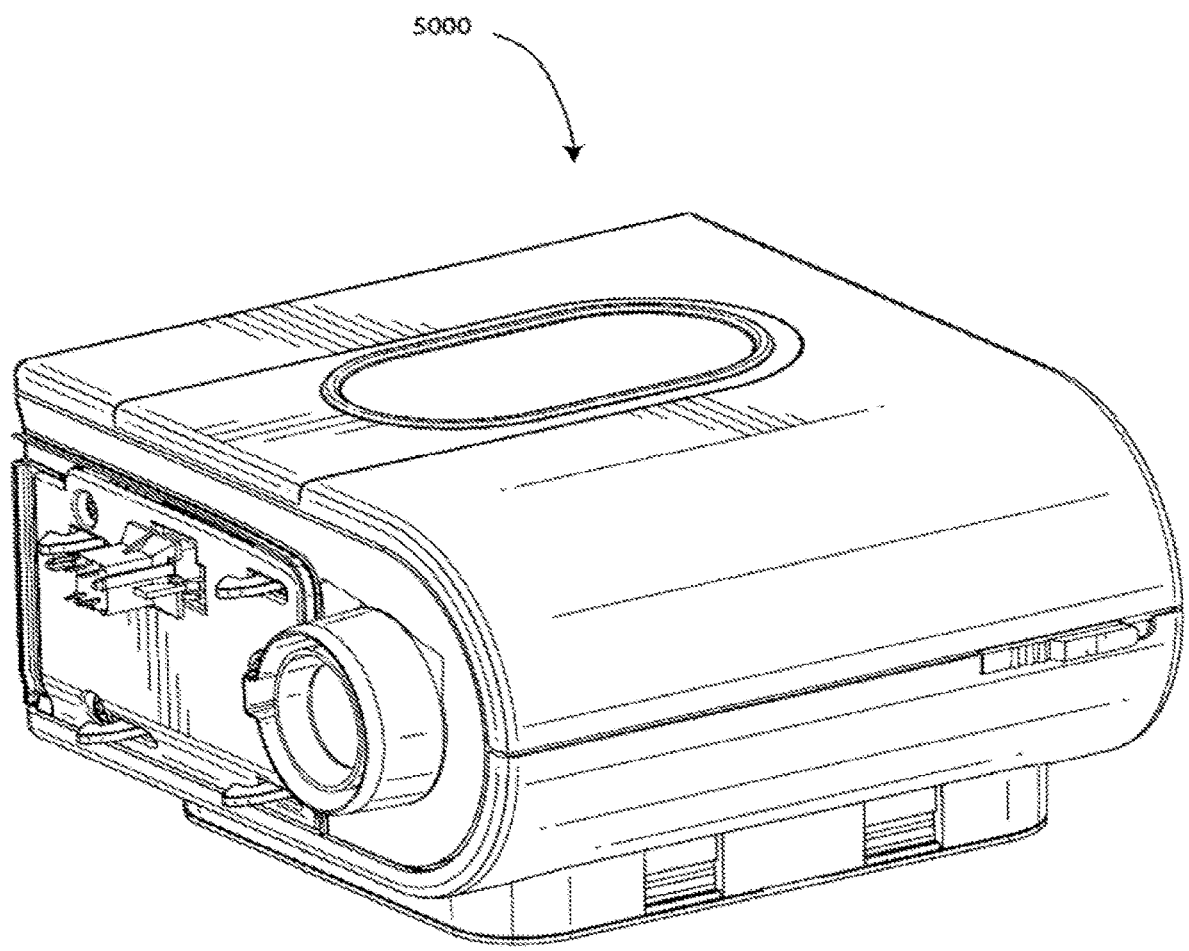

FIG. 6A shows a humidifier in accordance with one aspect of the present technology.

Figure 6B:
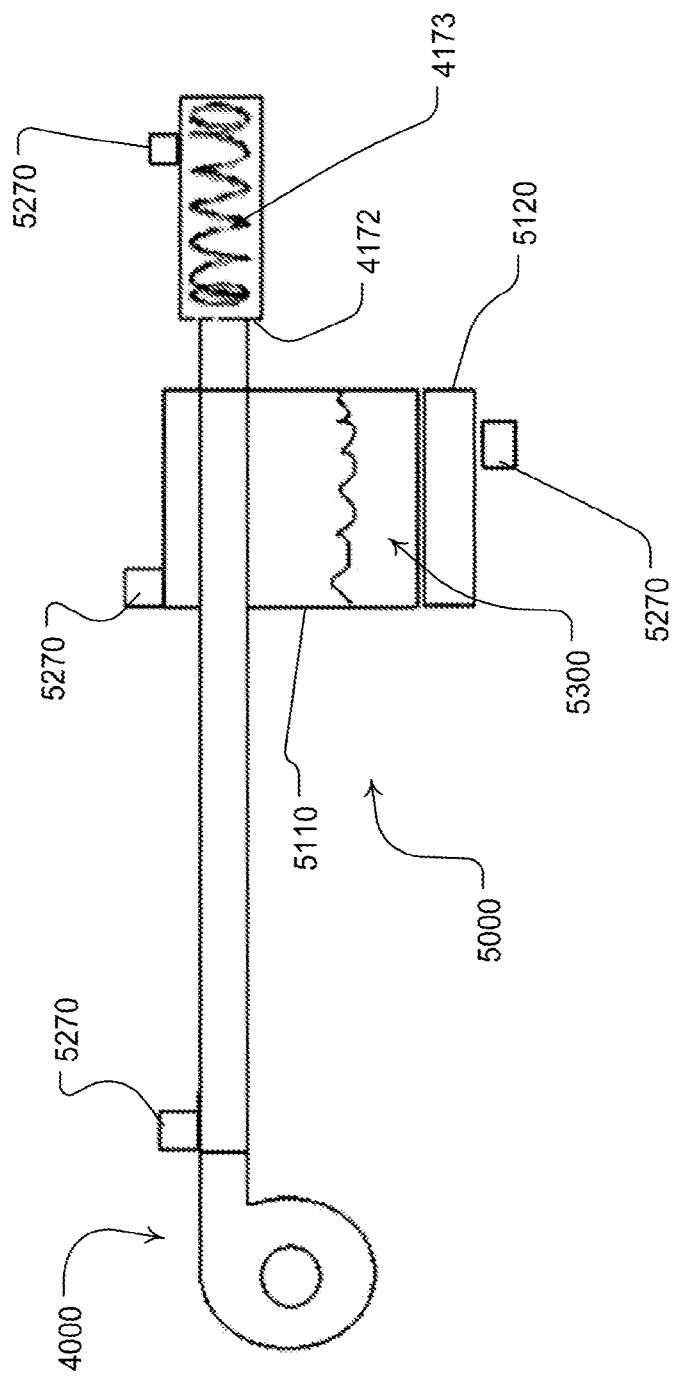

FIG. 6B shows a schematic of a humidifier.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

8.1 Switched Reluctance Motor

8.1.1 Stator

In one form, the present technology comprises a switched reluctance motor including a stator having distributed coil windings. In a case of a distributed windings configuration, the coils are placed or wound into the slots. With such a distributed winding, each coil winding may encircle or encompass at least two stator teeth (or more) while skipping over at least one stator slot (or more). The coils may have full pitch or fractional pitch. The number of slots that are occupied with the coils of one phase depend on the number of rotor poles and a winding distribution parameter. The winding distribution parameter indicates how many adjacent slots are occupied with coil segments of the same phase.

Figure 2A:
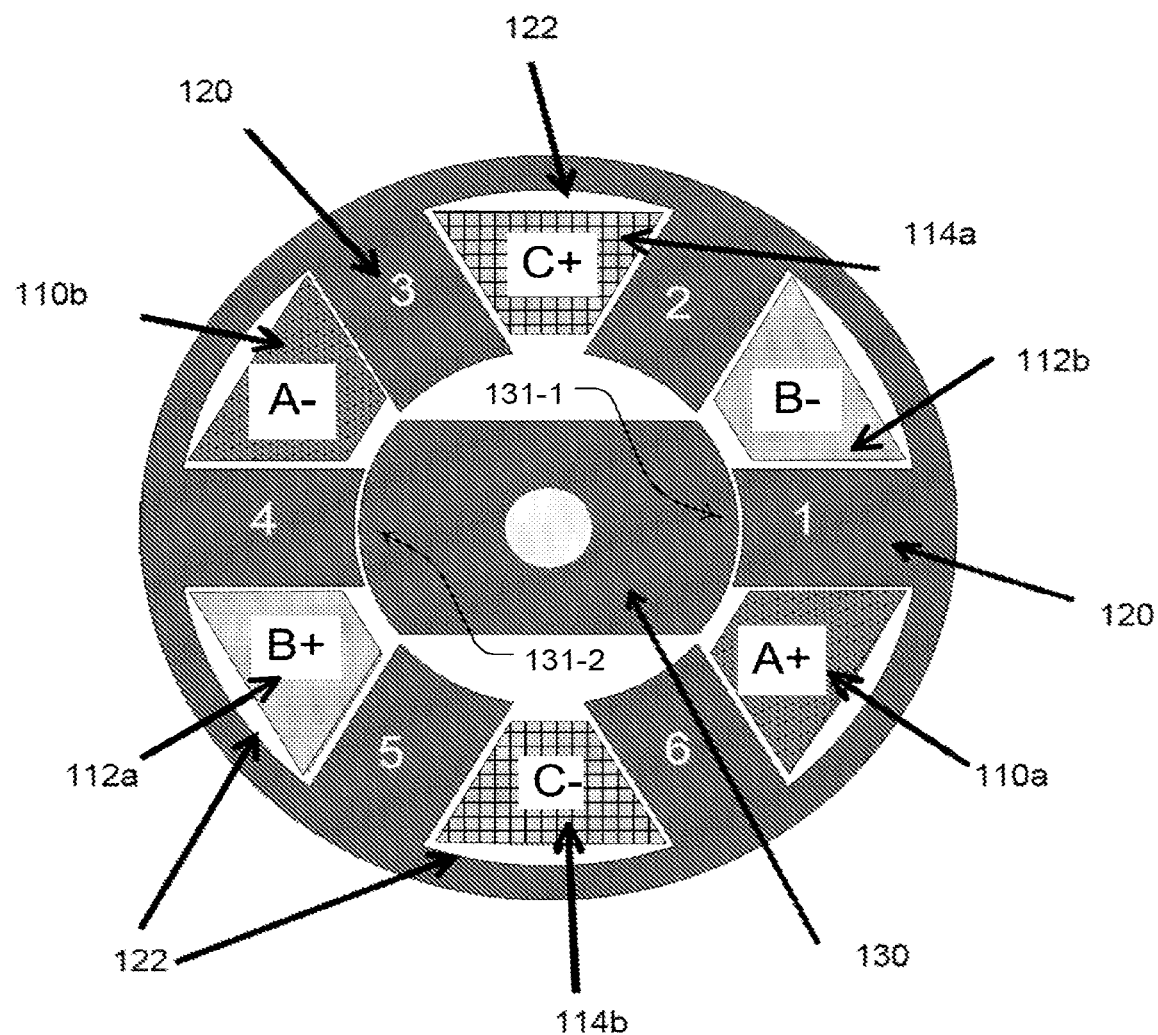
FIG. 2A shows an exemplary switched reluctance motor 6/2 stator and rotor configuration with distributed windings in accordance with another aspect of the present technology.
Figure 2B:
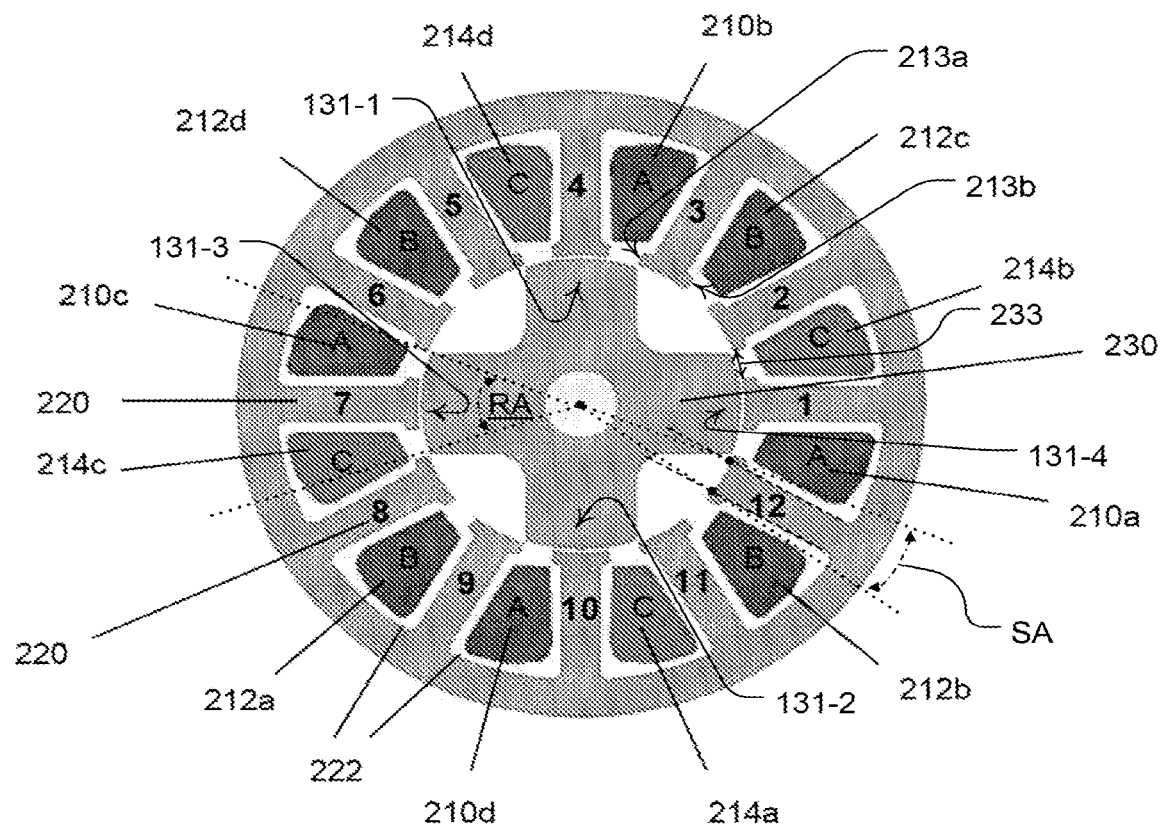
FIG. 2B shows an exemplary switched reluctance motor 12/4 stator and rotor configuration with distributed windings in accordance with one aspect of the present technology.

In the exemplary stator assemblies as shown in FIGS. 2A and 2B the winding distribution parameter is 1 as each coil segment (i.e., the coil portion within a stator slot) for each phase is adjacent a coil segment from another phase and not adjacent another coil segment from the same phase. There may be one or more coils for the same phase and coils from the same phase are referred to as a coil group. Each coil group comprises at least one coil, such as one, two, three, four, five or more coils per coil group. Each of the coils in a coil group includes two coil segments (i.e. a pair of coil segments) provided in different stator slots.

FIG. 2A shows a stator and rotor configuration for a three phase SR motor having 6 stator poles (6 stator teeth 120 and 6 stator slots 122) and 2 rotor poles 130 according to an example of the present technology. In FIG. 2A, each phase includes one coil for each phase and the coil is wound with two coil segments within two stator slots 122. The segments are connected by the end turns of the winding which is not shown in the figure. The A phase coil includes A+ and A− coils segments 110a, 110b respectively located within stator slots between stator teeth 1 & 6 and stator teeth 3 & 4 respectively. The B phase coil includes B+ and B− coil segments, 112a, 112b respectively that are located within stator slots between stator teeth 4 & 5 and stator teeth 1 & 2 respectively. The C phase coil includes C+ and C− coil segments 114a, 114b respectively that are located within stator slots between stator teeth 2 & 3 and stator teeth 5 & 6. Thus, each stator coil is located in a slot between two stator teeth and adjacent winding coils from different phases share an association with stator teeth that separate them. In this configuration, each stator coil segment from the same phase is separated from the other stator coil segment of the same phase by three stator teeth. The coils are not wound around a single stator tooth.

Figure 2C:
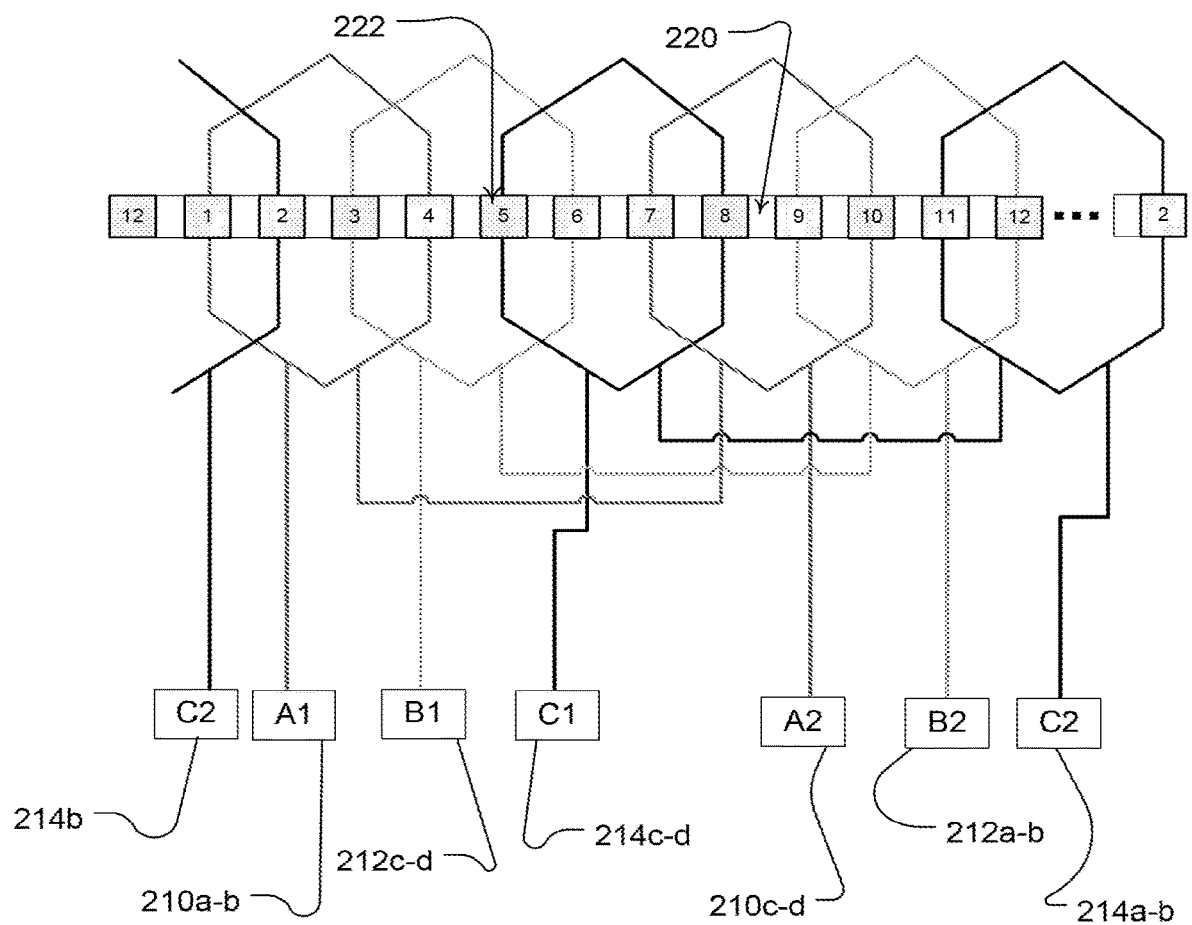
FIG. 2C illustrates the winding configuration of the exemplary SR motor shown in FIG. 2B.

FIGS. 2B and 2C illustrate a stator and rotor configuration for a three phase SR motor having 12 stator poles (12 stator teeth 220 and 12 stator slots 222) and 4 rotor poles 230 according to another example of the present technology. In FIG. 2C the slots are numbered "1" through "12" and each tooth, although not shown with a number, may be considered to have the same number as the numbered slot to the left of the tooth. (i.e., stator tooth 1 is between stator slots 1 and 2, etc.) In this arrangement there are two coil winding groups for each phase, each group includes one coil formed of two coil segments that occupy two stator slots. The coil segments are distributed evenly around the stator and each coil segment for a single phase is separated by three stator teeth. In FIG. 2C, stator slots numbered 2 and 12 and coil 214*b* are each shown twice simply for purposes of more clearly illustrating the coil windings pattern. For example, phase A coil segments 210*a* and 210*b* are separated by stator teeth 1, 2 and 3 are wound through slots numbered 1 and 4 to be located in slots 1 and 4. In the illustrated example phase A coil segments 210*a*, 210*b*, 210*c* and 210*d* are located in stator slots 1, 4, 7 and 10, between stator teeth 12 and 1; 3 and 4; 6 and 7; and 9 and 10 respectively. Phase B coil segments 212*a*, 212*b*, 212*c* and 21*d* are located in slots 9, 12, 3 and 6, between stator teeth 8 and 9; 11 and 12; 2 and 3; and 5 and 6 respectively. Phase C coil segments 214*a*, 214*b*, 214*c* and 214*d* are located in slots 11, 2, 5 and 8, between stator teeth 10 and 11; 1 and 2; 4 and 5; and 7 and 8 respectively. Thus, each stator slot includes a single coil segment from one coil. A skilled addressee would appreciate that the coils or coil segments for the different phases may be arranged in a different order.

Although FIGS. 2A and 2B refer to three phase motors (i.e., phases A B and C), it is to be understood that the motor may comprise a different number of phases such as two, four, five or more phases. The number of stator slots or stator teeth for different SR motor configurations may be determined as a function of the number of phases and the number of rotor poles. The winding distribution parameter may also be used in this determination for example using the following equation:

Total number of stator slots=number of phases×number of rotor poles×winding distribution parameter.

Thus, the total number of stator slots may be a multiple of number of phases and number of rotor poles of the motor. Moreover, the total number of stator slots may be a multiple of a winding distribution parameter.

The stator is formed as a lamination stack for example of steel laminations such as silicon steel e.g. M19 grade silicon steel (M19_29G). The rotor may be formed of the same material as the stator or another type of ferromagnetic material like ferrite or iron cobalt alloys. The coils may be formed of any wire gauge preferably in the range of 26 to 32 gauge wire, for example, each of the coils may be formed from American wire gauge (AWG) 30. The number of turns of the wire is determined by the voltage of the motor. For example the coils may include 30-40 turns per coils such as 34 turns per coil. In some cases, each turn of the coil may have one or more wires in hand such as a number in a range of 2 to 10 wires in hand per turn. For example, it may have six wires in hand per turn. Thus, in one example winding, the wire may be AWG 30, and each coil may have 34 turns with 6 wires in hand. However, a skilled addressee would understand that the coils may be formed of other material and include a different number of turns per coil and number of wires etc.

Figure 1:
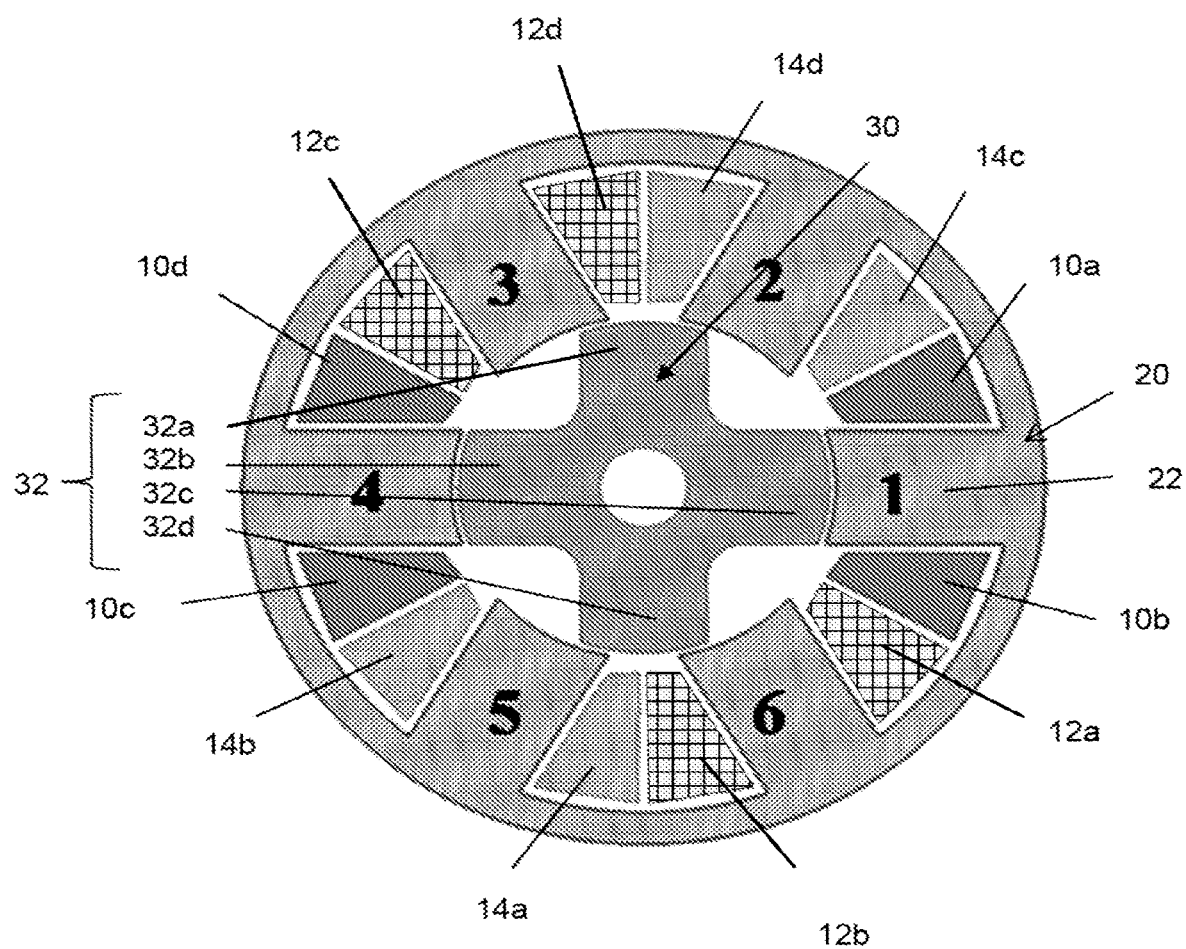
FIG. 1 shows an example of a prior art switched reluctance motor 6/4 stator and rotor configuration with concentrated windings.

A SR motor having a distributed winding configuration distributes the flux between the teeth that each of the phase coils is associated rather than concentrating the flux in a single stator tooth. This results in the radial electromagnetic forces acting between the stator and the rotor being distributed along the stator teeth that are associated with the energized coils. Thus, in the three phase stator arrangement illustrated in FIG. 2B the electromagnetic force is applied to four teeth with a 90° mechanical phase shift at the same time, see FIGS. 2G to 2R. In contrast a conventional three phase concentrated stator as in FIG. 1 applies the electromagnetic force to two teeth with a 180° phase shift at the same time. Therefore in the exemplary SR motor with distributed windings the peak radial force applied to each tooth is less than in a conventional concentrated winding. In other words, the distribution permits a reduction in radial forces. For example in a SR motor comprising a 12/4 rotor configuration as illustrated in FIG. 2B the peak radial force in each tooth may be 329 Newtons compared to 518N per tooth in a 6/4 concentrated winding conventional SR motor as illustrated in FIG. 1. The distribution of the radial electromagnetic forces reduces vibration and consequently reduces noise produced from the SR motor.

The SR motor including a distributed winding configuration of the present technology may have a low aligned to unaligned inductance ratio, such as an inductance ratio of less than 3, or less than 2.5 e.g. between 2 and 2.5.

Advantageously the SR motor including a distributed winding configuration according to the present technology allows for smaller lower power SR motors to be made that produce enough torque to run small high speed devices (up to 60,000 rpm). A small SR motor is understood to mean a SR motor having a stator outer diameter of less than 50 mm, such as 48 mm, 47 mm, 46 mm, 45 mm, 44 mm, 43 mm or less. However, it is to be understood that a SR motor having a distributed winding configuration may also be used in larger motors than have stator outer diameters greater than 50 mm.

8.1.2 Rotor

The rotor includes at least two rotor poles 130, 230, the rotor poles form rotor teeth that extend out from a central rotor core. In FIG. 2A, the rotor has two rotor teeth 131-1, 131-2. In FIG. 2B, the rotor has four rotor teeth 131-1, 131-2, 131-3, 131-4. Each of the rotor teeth may have a width that is wider than the width of a single stator tooth. This can help to distribute the radial electromagnetic forces acting between the stator and the rotor between multiple stator teeth that are associated with the energized coils. In this example of FIG. 2B, the width of a rotor tooth may be approximately equal to the width of a stator tooth (e.g., the length of the inner arc surface of an end of the stator tooth) plus some width such as a function of a measure of the width of the gap between adjacent stator teeth. The gap 233 being the stator slot width at the inner end of the stator slot (the inner end being the end closest to the rotor). For example, the width of a rotor tooth may be approximately equal to the width of the stator tooth plus a multiple (e.g., two times) of the width of the gap between stator teeth. In this regard, the rotor width may be understood to refer to a length along a surface at an end of the rotor tooth that may be formed as an arc at an end of each tooth of the rotor.

In some versions of the present technology, each stator tooth may have tooth tips 213*a*, 213*b* (labeled in FIG. 2B) that form projections on either side of a stator tooth and that extend the width of the stator while still permitting a gap between the stator teeth. The teeth tips can serve to smooth the field in air gap between stator teeth and help to reduce noise. The tips may also help with keeping the winding in the gap or helping to prevent the winding from shifting to the rotor area of the bore. In some versions of the present technology, a suitable stator tooth width may be about 2.4 mm. However, other widths may be employed, such as a width in a range of 1.75 mm to 5 mm. That stator tooth width may increase by the width of the tooth tips when included. In some cases, the rotor pole width may be about 7 mm. However, other widths may be employed, such as a width in a range of 5 mm to 10 mm.

The central angles of the stator and rotor poles may be as significant as absolute width values of the teeth. For example, in some typical motor designs, the central angle of the stator and rotor poles may be approximately the same or have a very small difference between them such as a few degrees. However, in some versions of the present technology, the angles may be significantly different, such as having an angle difference of more than several degrees (e.g., more than 5 degrees such as in a difference range from 3 degrees to 40 degrees, or such as in a difference range of 5 degrees to 30 degrees. For example, the stator central angle, such as the angle formed from the center of the stator with imaginary lines extending radially to the edges of a stator's tooth or stator's tips (see, e.g., angle SA illustrated in FIG. 2B) may be about 13 degrees (e.g., 13.12°). In such an example, the rotor central angle, such as the angle formed from the center of the rotor with imaginary lines extending radially to the edges of a rotor's tooth (see, e.g., angle RA illustrated in FIG. 2B) may be about 40 degrees (e.g., 40.14°). Such a difference between the stator central angle and rotor central angle is very significant (e.g., approximately 27 degrees).

The rotor may be formed of a suitable material such as silicon steel e.g. M19 grade silicon steel (M19_29G) or another type of ferromagnetic material like ferrite or iron cobalt alloys.

8.1.3 Motor Control

Figure 2D:
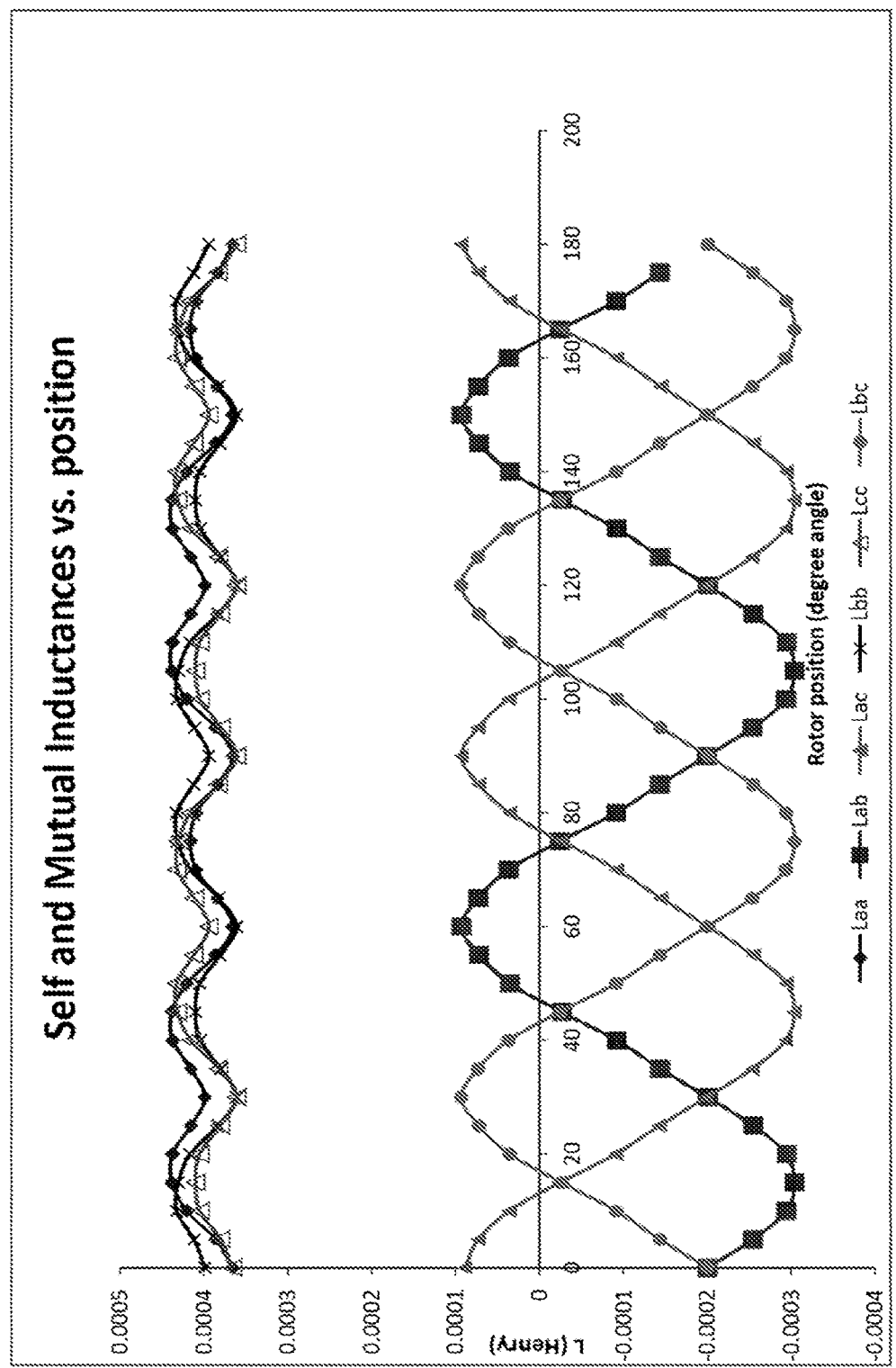
FIG. 2D illustrates the self and mutual inductances versus the mechanical angle of the rotor of the exemplary SR motor of FIG. 2B.

As mentioned previously, torque in SR motors is proportional to the difference in a phase self-inductances in an aligned and non-aligned position when the appropriate phase is energized. It has been determined that using a distributed stator winding configuration in a SR motor of the present technology may produce a significant mutual inductance variation between certain positions of the rotor. This mutual inductance may be utilized to produce a higher torque at small power (less than hundred watts such as 90 Watts, 60 Watts or 50 Watts) SR motor design. FIG. 2D illustrates an example of the self and mutual inductances produced in a SR motor according to the present technology. The self-inductances Laa, Lbb and Lcc show significantly less variation in the inductance generated at the different rotor positions than the mutual inductances Lab, Lac and Lbc. The mutual inductance variation is approximately eight times the variation range generated by the self-inductances in the example shown. As torque is proportional to the difference of align and non-align values of the inductance in SR motors the mutual inductance may be utilised to produce a larger portion of the torque. The total torque produced in the motor is the sum of the components related to self-inductance and the mutual inductance.

The stator of the SR motor of the present technology includes at least three motor phases. Due to the mutual inductance producing a large portion of the torque, the SR motor of the present technology may be configured to energize two phases at the same time during each conduction period. A first phase may be energized with a positive direction current and a second phase may be energized with a negative direction current resulting in a net flux increase in the motor and producing a higher torque. Two phases are energised at the same time and follow a specific sequence to cause the rotor to rotate. Each phase of the motor may be energized with the same current value during at least two consecutive conduction periods. For example in some configurations one of the two energized phases is switched off to a non-energized state and one of the non-energized phases is switched on to an energized state during each commutation period. The timing of the commutation period or switching is controlled to facilitate smooth rotation of the motor and reduce cogging.

Figure 2E:
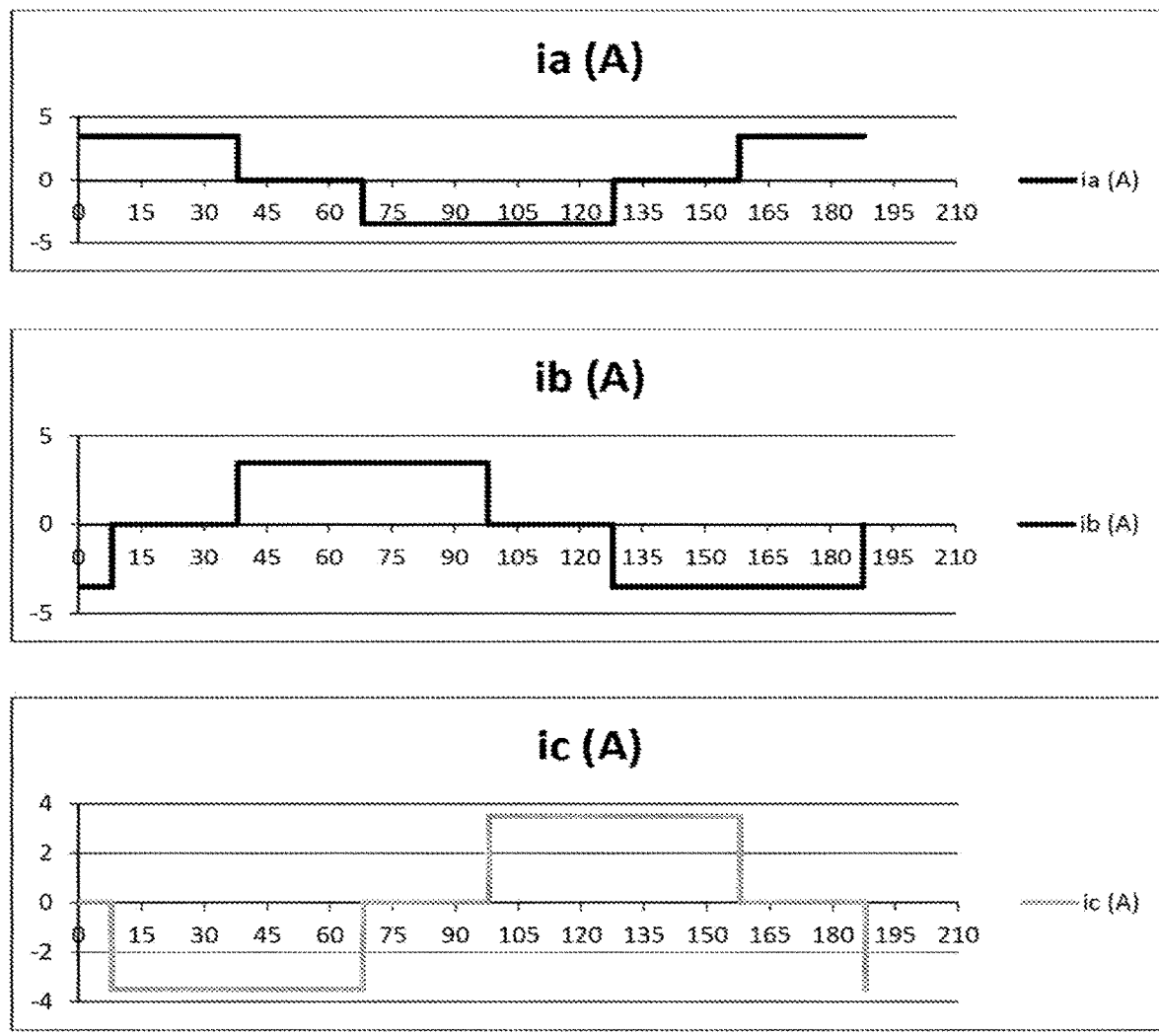
FIG. 2E illustrates an exemplary pattern of applying current to the different phases of the SR motors of FIG. 2B.

FIG. 2E shows an exemplary commutation for a SR motor comprising a distributed stator as shown in FIG. 2B. In a first step phase A may be energised with a positive direction current, phase B may be energised with a negative direction current and phase C may be non-energised (zero current) (i.e., A+B−). This will cause the rotor to move towards the alignment position shown in FIG. 2H. In the second step, phase A may continue to be energised with a positive direction current, phase B is switched off to an non-energized state (zero current) and phase C is energized with a negative direction current (i.e. A+C−). This will cause the rotor to move towards the alignment positions shown in FIG. 2J. In the third step, the phase A is switched off to an non-energized state (zero current), phase B is energized with a positive direction current and phase C continues to be energized with a negative direction current (i.e. B+C−). This will cause the rotor to move towards the alignment position shown in FIG. 2L. This sequential switching of the phases continues such that the fourth step would be B+A− causing the rotor to move towards the alignment position shown in FIG. 2N. The fifth step, C+A−, causing the rotor to move towards the alignment position shown in FIG. 2P. The sixth step, C+B−, causing the rotor to move towards the alignment position shown in FIG. 2R. Then the cycle repeats again by returning to A+B− to provide a full 360° revolution of the rotor. The specific timing of the switching or commutation of the energization of the phases may be varied to adjust the performance of the motor and reduce torque ripple.

Figure 2F:
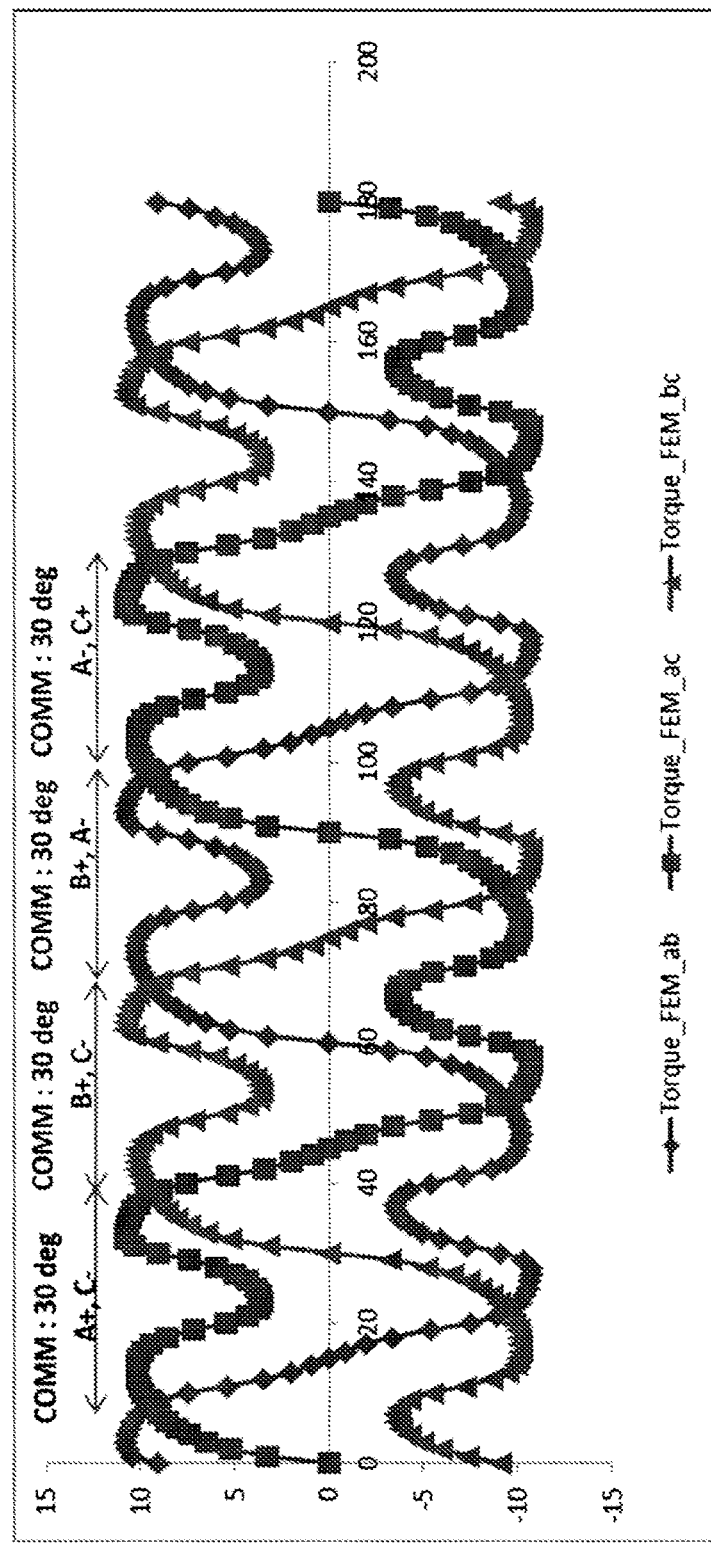
FIG. 2F illustrates the torque produced by the exemplary SR motor in FIG. 2B for different current sequences.
Figure 2G:
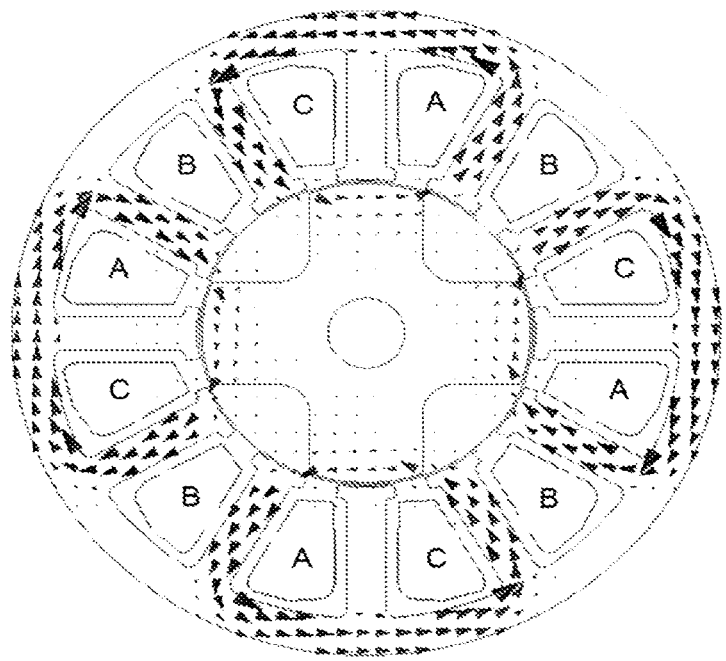
FIG. 2G illustrates exemplary flux paths for a rotor mechanical angle of 0°, 180° and 360° as the minimum mutual inductance position when phase A is provided with positive current and phase C is provided with negative current for the SR motor of FIG. 2B.
Figure 2H:
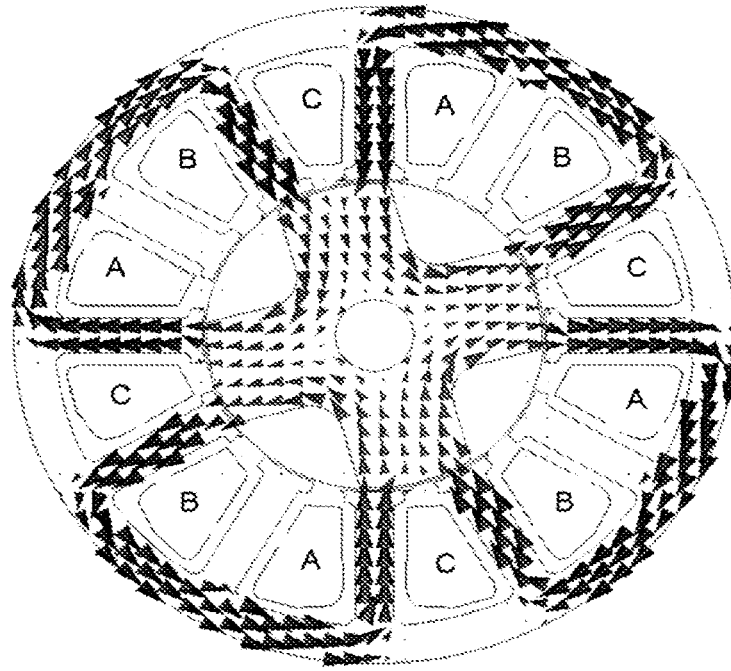
FIG. 2H illustrates exemplary flux paths for a rotor mechanical angle of 15° and 195° as the maximum mutual inductance position when phase A is provided with positive current and phase B is provided with negative current for the SR motor of FIG. 2B.
Figure 2I:
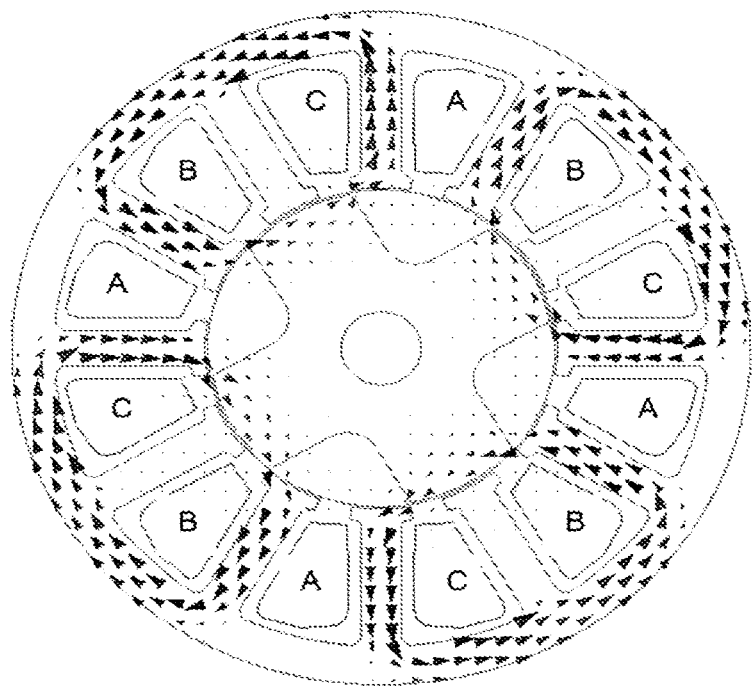
FIG. 2I illustrates exemplary flux paths for a rotor mechanical angle of 30° and 210° as the minimum mutual inductance position when phase B is provided with positive current and phase C is provided with negative current for the SR motor of FIG. 2B.
Figure 2J:
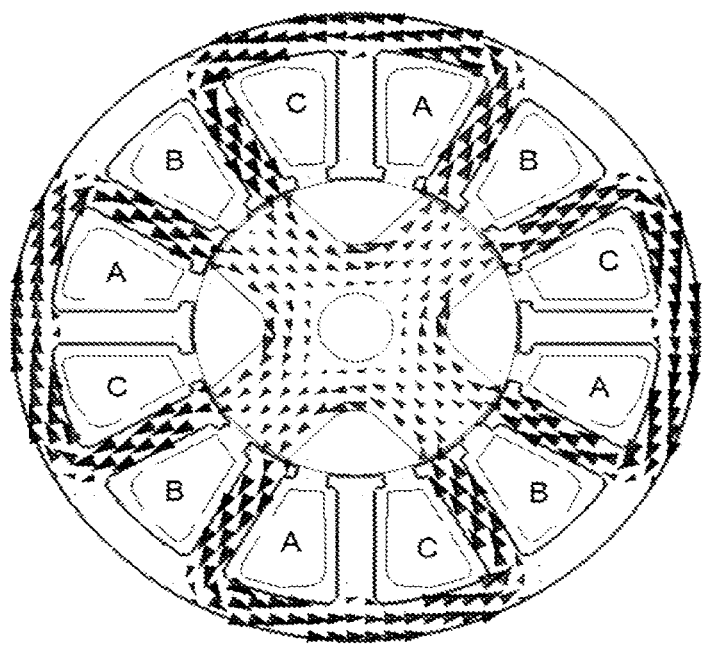
FIG. 2J illustrates exemplary flux paths for a rotor mechanical angle of 45° and 225° as the maximum mutual inductance position when phase A is provided with positive current and phase C is provided with negative current for the SR motor of FIG. 2B.
Figure 2K:
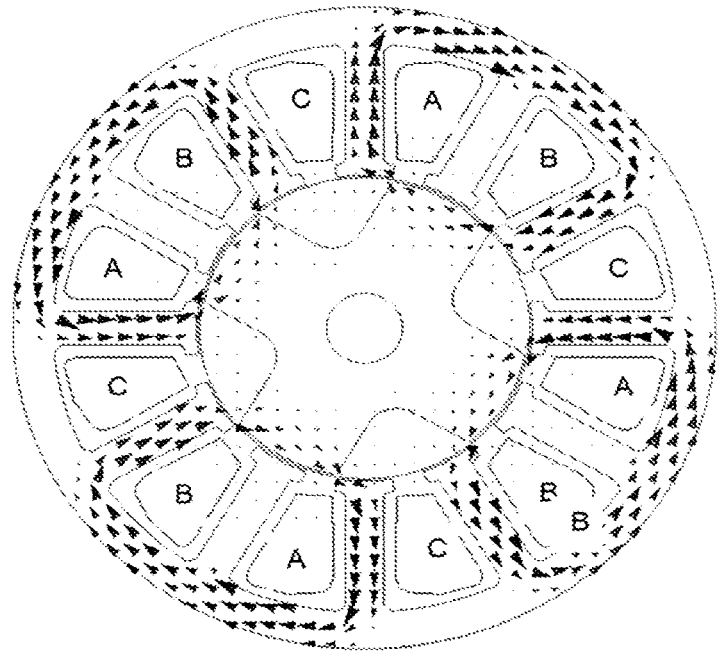
FIG. 2K illustrates exemplary flux paths for a rotor mechanical angle of 60° and 240° as the minimum mutual inductance position when phase B is provided with positive current and phase A is provided with negative current for the SR motor of FIG. 2B.
Figure 2L:
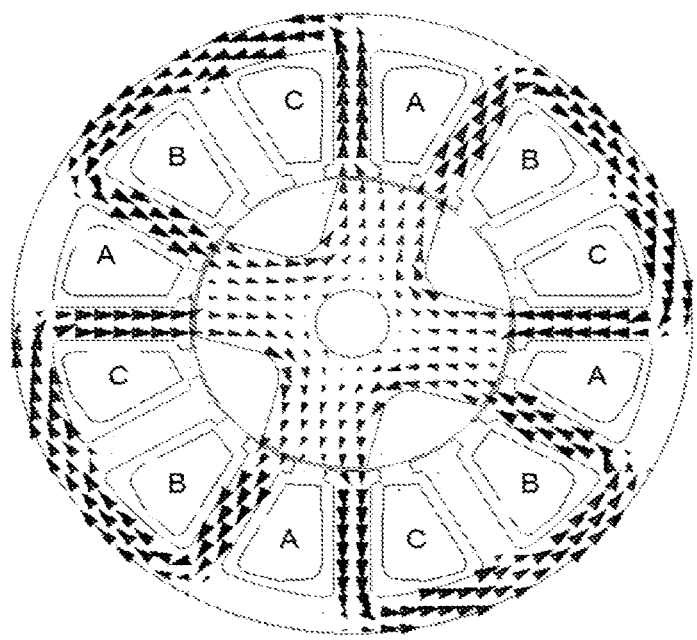
FIG. 2L illustrates exemplary flux paths for a rotor mechanical angle of 75° and 255° as the maximum mutual inductance position when phase B is provided with positive current and phase C is provided with negative current for the SR motor of FIG. 2B.
Figure 2M:
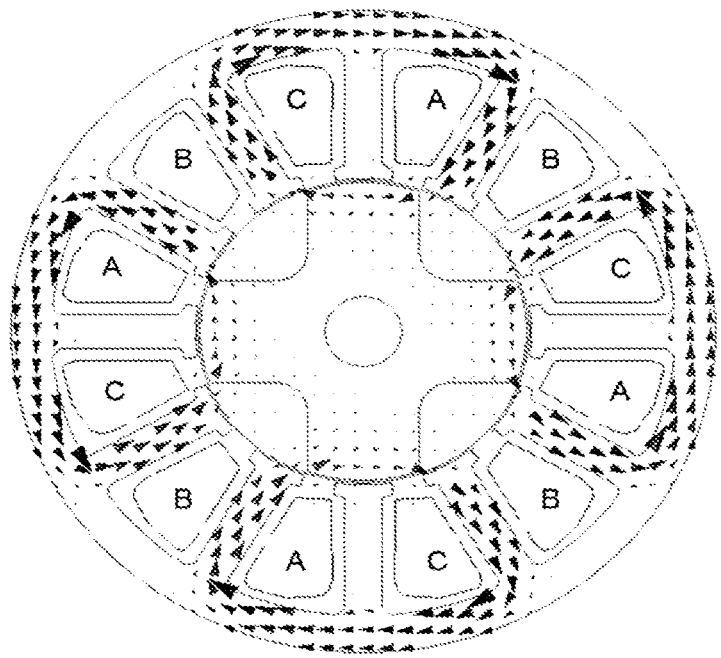
FIG. 2M illustrates exemplary flux paths for a rotor mechanical angle of 90° and 270° as the minimum mutual inductance position when phase C is provided with positive current and phase A is provided with negative current for the SR motor of FIG. 2B.
Figure 2N:
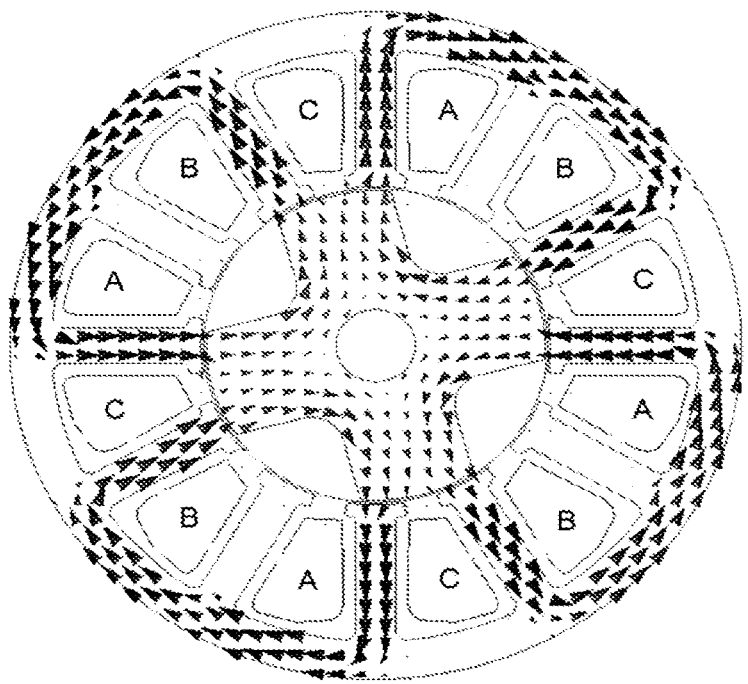
FIG. 2N illustrates exemplary flux paths for a rotor mechanical angle of 105° and 285° as the maximum mutual inductance position when phase B is provided with positive current and phase A is provided with negative current for the SR motor of FIG. 2B.
Figure 2O:
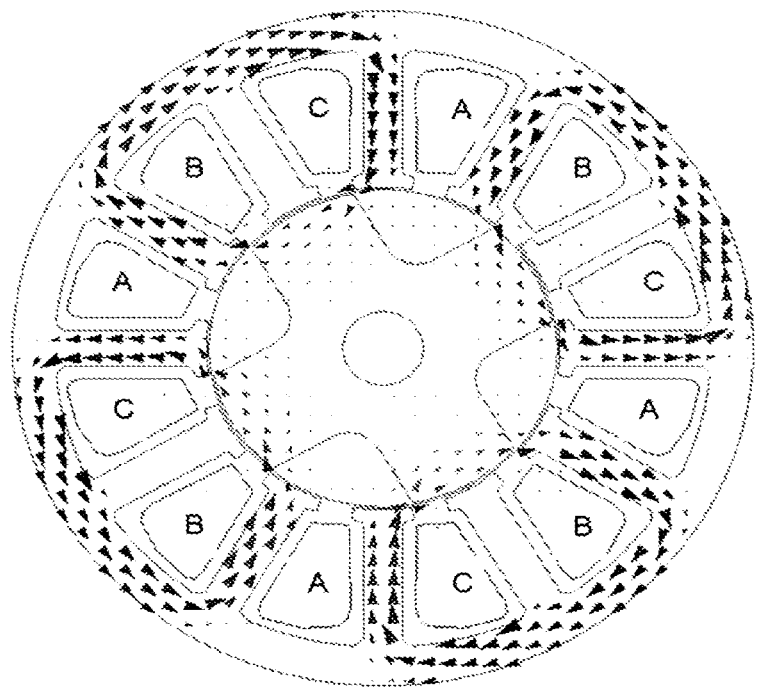
FIG. 2O illustrates exemplary flux paths for a rotor mechanical angle of 120° and 300° as the minimum mutual inductance position when phase C is provided with positive current and phase B is provided with negative current for the SR motor of FIG. 2B.
Figure 2P:
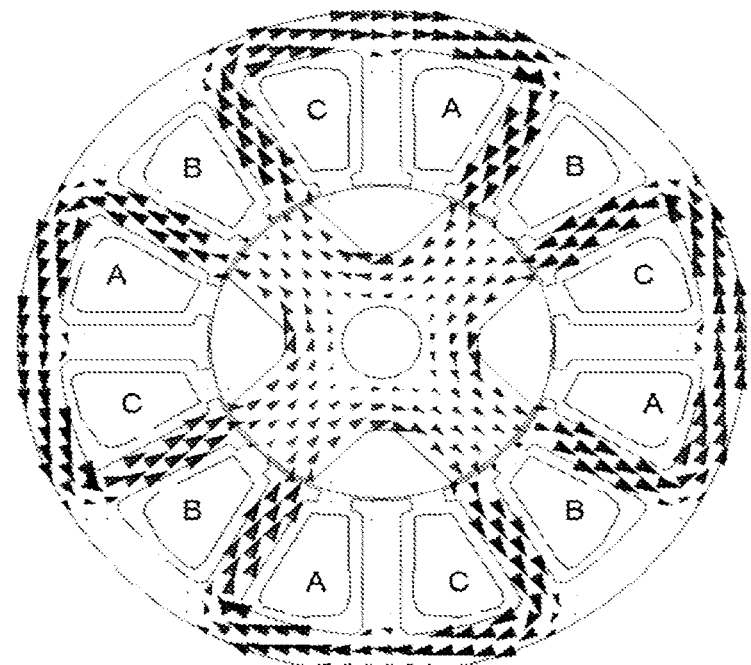
FIG. 2P illustrates exemplary flux paths for a rotor mechanical angle of 135° and 315° as the maximum mutual inductance position when phase C is provided with positive current and phase A is provided with negative current for the SR motor of FIG. 2B.
Figure 2Q:
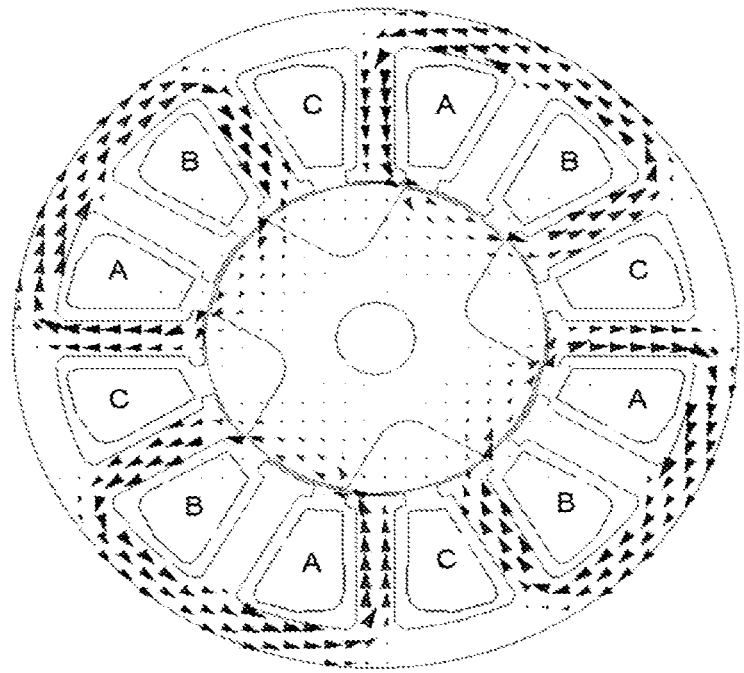
FIG. 2Q illustrates exemplary flux paths for a rotor mechanical angle of 150° and 330° as the minimum mutual inductance position when phase A is provided with positive current and phase B is provided with negative current for the SR motor of FIG. 2B.
Figure 2R:
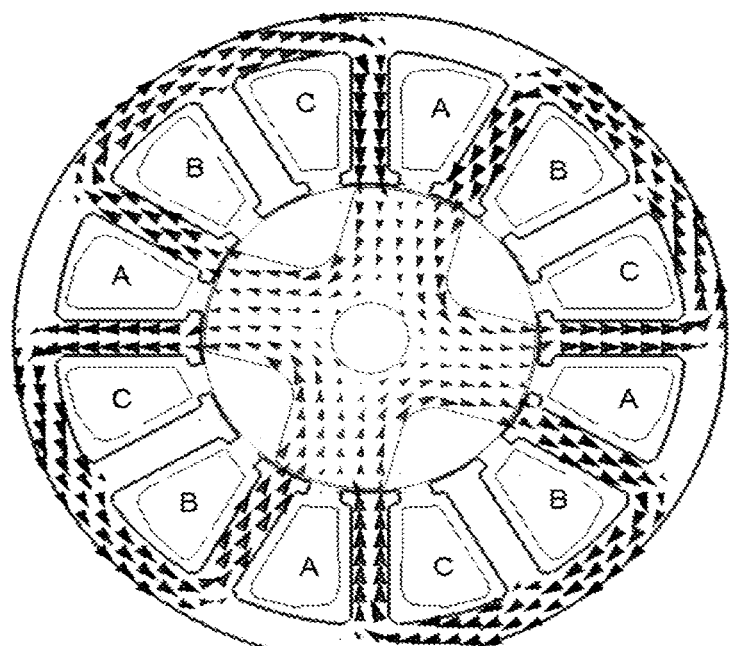
FIG. 2R illustrates exemplary flux paths for a rotor mechanical angle of 165° and 345° as the maximum mutual inductance position when phase C is provided with positive current and phase B is provided with negative current for the SR motor of FIG. 2B.

FIG. 2F shows an example of the torque produced for different current sequences relative to the rotor position in a SR motor comprising a stator and rotor configuration as shown in FIG. 2B. For example for a rotor position between 8° to 38°, the slope of Lac produces the largest proportion of the torque.

$$T_a = \frac{1}{2}\frac{\partial L_{aa}}{\partial \theta}i_a^2 + \frac{\partial L_{ab}}{\partial \theta}i_a i_b + \frac{\partial L_{ac}}{\partial \theta}i_a i_c,$$

Where Ta the instantaneous torque value, $i_a$, $i_b$ and $i_c$ are instantaneous values of the current in phases A, B and C respectively. $L_{aa}$ is the total inductance of phase A. $L_{ab}$ is the mutual inductance between phases A and B and $L_{ac}$ is the mutual inductance between phases A and C respectively.

In contrast in a conventional SR motor, where only the self-inductance component is producing the torque, i.e.

$$T_a = \left(\frac{1}{2}\frac{\partial L_{aa}}{\partial \theta}i_a^2\right).$$

A method of controlling a switched reluctance motor comprising at least three phases may include during each conduction period energizing a first phase with a negative direction current, energizing a second phase with a positive current and having at least one non-energized phase and during each commutation period switching off one of the first phase or the second phase to a non-energized state and switching on one of the non-energized phases to an energized state with the same direction current as the first or second phase that was switched off. The switched reluctance motor may include a distributed winding configuration as described above.

In some aspects of the present technology the SR motor may be controlled using a sensorless control. In this arrangement when the rotor passes the non-energized phase, the back EMF, induced in the phase can be detected and filtered in order to remove the noise. The signal is proportional to the rotor angle and may be used to estimate the position of the rotor.

8.1.4 Motor Assembly

An example of a motor assembly 3002 that may be implemented with the switched reluctance motor technology described herein is illustrated in FIGS. 3A through 3J. As seen in FIGS. 3A and 3B, the motor assembly 3002 may include a motor housing 3100, an end bell 3110 and one or more impeller(s) 3120. An example end bell is shown in FIGS. 3C and 3D. An example motor housing is illustrated in FIGS. 3E and 3F. The motor assembly may also optionally include an encoder 3130, such as an optical encoder to detect rotation and/or positioning (e.g., absolute or relative movement) of the shaft of the rotor assembly. As seen in FIG. 3B, a housing of the encoder may be coupled to the end bell 3110 with one or more fasteners, such as screws 3132a. Corresponding fastener holes 3135 on the end bell 3110 and motor housing 3100 as seen in FIGS. 3A, 3C, 3D and 3F receive additional fasteners, such as screws 3132b etc., for joining and holding the end bell 3110 and motor housing 3100 together. Other types of fasteners may also be implemented such as bolts, snap fit structures, clips, rivets, etc. for joining the structures of the motor assembly. As shown in FIG. 3f, the motor housing may optionally include a wiring aperture 3235. The wiring aperture can permit lead wires of the coils of the stator assembly to pass out of the motor assembly when the stator assembly is installed within the motor assembly.

As seen in more detail in the cross sectional view of FIG. 3B, the motor housing 3100 and end bell 3110 may contain the stator assembly 3140 and rotor assembly 3150 (on FIG. 3G). (the rotor assembly 3150 is not shown in FIG. 3B). The stator assembly 3140 may include a stator 3141 and coils in any configuration as previously described such as the stator configuration illustrated in FIG. 2B. As illustrated in FIG. 3H, the stator 3141 of such a stator assembly, like the rotor, can be formed in a laminated stack. An example coil configuration is illustrated in FIGS. 3I and 3J showing the stator 3141 with stator teeth 220 and stator slots 222. Coil groups for phases A, B and C are shown.

The rotor assembly 3150 may include a rotor in any configuration as previously described such as the rotor configuration also illustrated in FIG. 2B. In this regard, the rotor assembly may include a rotor 3152 and shaft 3154 as illustrated in FIG. 3G. As illustrated, the rotor may be a laminated rotor stack (e.g., a plurality of stacked plates) that are bonded to the shaft using a primer and adhesive. The rotor assembly may be mounted for rotation within the motor housing 3100 and end bell 3110 with a set of bearings 3160a, 3160b through which the shaft ends are inserted. The bearings 3160a, 3160b may each reside in a cylindrical bearing seat 3161a, 3161b in each of the end bell 3110 and the motor housing 3100 respectively. The shaft may also be positioned within the assembly with a spring 3162. The impeller(s) 3120 may be press fit at an impeller end of the shaft 3154 opposite an encoder end of the shaft 3154. Alternatively, the shaft may have impellers at both ends of the shaft (not shown). The rotor assembly may also include one or more balance rings 3164a, 3164b. The motor assembly or the impeller(s) may be inserted or positioned within a volute such as the example volute illustrated in FIG. 5A so that the motor assembly may serve as part of a blower of a flow generator.

8.2 Treatment Systems

In one form, the present technology comprises apparatus for treating a respiratory disorder. The apparatus may comprise a flow generator or blower including a switched reluctance motor for supplying pressurised respiratory gas, such as air, to the patient 1000 via an air delivery tube 4170 leading to a patient interface 3000.

8.3 Therapy

In one form, the present technology comprises method for treating a respiratory disorder comprising the step of applying positive pressure to the entrance of the airways of a patient 1000 using a pressure device including a switched reluctance motor.

8.3.1 Nasal CPAP for OSA

In one form, the present technology comprises a method of treating Obstructive Sleep Apnea in a patient by applying nasal continuous positive airway pressure to the patient using a patient interface.

In certain embodiments of the present technology, a supply of air at positive pressure is provided to the nasal passages of the patient via one or both nares.

A patient interface 3000 is provided as seen in FIG. 4 to deliver the supply of pressurized air to the patient's airways. A number of different types of patient interfaces including non-invasive and invasive interfaces are available. For example non-invasive masks include a nasal mask, full face mask, nasal prongs and nasal pillows and invasive interfaces include a tracheostomy tube. Non-invasive patient interfaces 3000 comprise a seal-forming structure to engage with a patient's face in use.

8.4 Pap Device 4000

As shown in FIGS. 5A to 5D a PAP device 4000 in accordance with one aspect of the present technology comprises mechanical and pneumatic components 4100, electrical components 4200 and is programmed to execute one or more algorithms 4300. The PAP device preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may optionally include a handle 4018.

The pneumatic path of the PAP device 4000 preferably comprises an inlet air filter 4112, an inlet muffler 4122, a controllable pressure device 4140 capable of supplying air at positive pressure (preferably a blower 4142) including a motor 4144, and an outlet muffler 4124. One or more transducers 4270 such as pressure sensors 4274, flow sensors 4272 and speed sensors 4276 are included in the pneumatic path.

The preferred pneumatic block 4020 comprises a portion of the pneumatic path that is located within the external housing 4010.

The PAP device 4000 may include an electrical power supply 4210, one or more input devices 4220, a central controller 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The central controller 4230 of the PAP device 4000 is programmed to execute one or more algorithm modules 4300, preferably including a pre-processing module 4310, a therapy engine module 4320, a therapy control module 4330, and further preferably a fault condition module 4340.

8.4.1 PAP Device Mechanical & Pneumatic Components 4100

8.4.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a blower 4142. See FIG. 5B.

In one form, an outlet air filter 4114, for example an antibacterial filter, is located between an outlet of the pneumatic block 4020 and a patient interface 3000. See FIG. 5B.

8.4.1.2 Muffler(s) 4120

In one form of the present technology, an inlet muffler 4122 is located in the pneumatic path upstream of a blower 4142. See FIG. 5B.

In one form of the present technology, an outlet muffler 4124 is located in the pneumatic path between the blower 4142 and a patient interface 3000. See FIG. 5B.

8.4.1.3 Pressure Device 4140

In a preferred form of the present technology, a pressure device 4140 for producing a flow of air at positive pressure is a controllable blower 4142. For example the blower may include a switched reluctance motor 4144 with one or more impellers housed in a volute. The blower may be preferably capable of delivering a supply of air, for example about 120 litres/minute, at a positive pressure in a range from about 4 cmH$_2$O to about 20 cmH$_2$O, or in other forms up to about 30 cmH$_2$O.

The pressure device 4140 is under the control of the therapy device controller 4240.

8.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

8.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

8.4.1.6 Air Circuit 4170

An air circuit 4170 in accordance with an aspect of the present technology is constructed and arranged to allow a flow of air or breathable gasses between the pneumatic block 4020 and the patient interface 3000.

8.4.1.7 Oxygen Delivery 4180

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

8.4.2 PAP Device Electrical Components 4200

8.4.2.1 Power Supply 4210

Power supply 4210 supplies power to the other components of the basic PAP device 4000: the input device 4220, the central controller 4230, the therapy device 4245, and the output device 4290.

In one form of the present technology, power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

8.4.2.2 Input device(s) 4220

A PAP device 4000 may include one or more input devices 4220. Input devices 4220 comprises buttons, switches or dials to allow a person to interact with the PAP device 4000. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

8.4.2.3 Central Controller or Processor 4230

In one form of the present technology, the central controller or processor 4230 is a dedicated electronic circuit configured to receive input signal(s) from the input device 4220, and to provide output signal(s) to the output device 4290 and/or the therapy device controller 4240.

In one form, the central controller 4230 is an application-specific integrated circuit. In another form, the central controller 4230 comprises discrete electronic components.

In one form of the present technology, the central controller 4230 is a processor suitable to control a PAP device 4000 such as an x86 INTEL processor.

A processor 4230 suitable to control a PAP device 4000 in accordance with another form of the present technology includes a processor based on ARM Cortex-M processor from ARM Holdings. For example, an STM32 series microcontroller from ST MICROELECTRONICS may be used.

Another processor 4230 suitable to control a PAP device 4000 in accordance with a further alternative form of the present technology includes a member selected from the family ARMS-based 32-bit RISC CPUs. For example, an STR9 series microcontroller from ST MICROELECTRONICS may be used.

In certain alternative forms of the present technology, a 16-bit RISC CPU may be used as the processor 4230 for the PAP device 4000. For example a processor from the MSP430 family of microcontrollers, manufactured by TEXAS INSTRUMENTS, may be used.

The processor 4230 is configured to receive input signal(s) from one or more transducers 4270, and one or more input devices 4220.

The processor 4230 is configured to provide output signal(s) to one or more of an output device 4290, a therapy device controller 4240, a data communication interface 4280 and humidifier controller 5250.

In some forms of the present technology, the processor 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a PAP device 4000. However, in some forms of the present technology the processor(s) may be implemented discretely from the flow generation components of the PAP device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

Preferably PAP device 4000 includes a clock 4232 that is connected to the central controller 4230.

8.4.2.4 Therapy Device 4245

In one form of the present technology, the therapy device 4245 is configured to deliver therapy to a patient 1000 under the control of the central controller 4230. Preferably the therapy device 4245 is a positive air pressure device 4140.

8.4.2.5 Therapy Device Controller 4240

In one form of the present technology, therapy device controller 4240 is a therapy control module 4330 such as for pressure control that forms part of the algorithms 4300 executed by the processor 4230.

In one form of the present technology, therapy device controller 4240 is a dedicated motor control integrated circuit. For example, in one form a MC33035 brushless DC motor controller, manufactured by ONSEMI is used.

8.4.2.6 Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

8.4.2.7 Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

8.4.2.8 Transducers 4270

Transducers may be internal of the device, or external of the PAP device. External transducers may be located for example on or form part of the air delivery circuit, e.g. the patient interface. External transducers may be in the form of non-contact sensors such as a Doppler radar movement sensor that transmit or transfer data to the PAP device.

8.4.2.8.1 Flow

A flow transducer 4272 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element. Other flow sensors may also be implemented such as a hot wire flow sensor.

In use, a signal representing total flow Qt from the flow transducer 4272 is received by the processor 4230.

8.4.2.8.2 Pressure

A pressure transducer 4274 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4274, is received by the processor 4230. In one form, the signal from the pressure transducer 4274 is filtered prior to being received by the processor 4230.

8.4.2.8.3 Motor Speed

In one form of the present technology a motor speed signal 4276 is generated. A motor speed signal 4276 is preferably provided by therapy device controller 4240. Motor speed may, for example, be generated by a speed sensor, such as a Hall effect sensor.

8.4.2.9 Data Communication Systems

In one preferred form of the present technology, a data communication interface 4280 is provided, and is connected to processor 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor 4230. In another form, data communication interface 4280 is an integrated circuit that is separate from processor 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

8.4.2.10 Output Devices Including Optional Display, Alarms

An output device 4290 in accordance with the present technology may take the form of one or more of a visual, audio, and haptic output. A visual output may be a Liquid Crystal Display (LCD) or Light Emitting Diode (LED) display. An audio output may be a speaker or audio tone emitter.

8.4.2.10.1 Display Driver 4292

A display driver 4292 receives as an input the characters, symbols, or images intended for display on the display 4294, and converts them to commands that cause the display 4294 to display those characters, symbols, or images.

8.4.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

8.4.3 PAP Device Algorithms 4300

8.4.3.1 Pre-Processing Module 4310

An pre-processing module 4310 in accordance with the present technology receives as an input, raw data from a transducer, for example a flow or pressure transducer, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation algorithm 4312, vent flow calculation algorithm 4314, leak flow algorithm 4316 and respiratory flow algorithm 4318.

A pressure compensation algorithm 4312 may receive as an input a signal indicative of the pressure in the pneumatic path proximal to an outlet of the pneumatic block. The pressure compensation algorithm 4312 estimates the pressure drop in the air circuit 4170 and provides as an output an estimated pressure, Pm, in the patient interface 3000.

A vent flow calculation algorithm 4314 may receive as an input an estimated pressure, Pm, in the patient interface 3000 and estimates a vent flow of air, Qv, from a vent 3400 in a patient interface 3000.

A leak flow algorithm 4316 may receive as an input a total flow, Qt, and a vent flow Qv, and provides as an output a leak flow Ql by calculating an average of Qt–Qv over a period sufficiently long to include several breathing cycles, e.g. about 10 seconds.

A respiratory flow algorithm 4318 may receive as an input a total flow, Qt, a vent flow, Qv, and a leak flow, Ql, and estimates a respiratory flow of air, Qr, to the patient, by subtracting the vent flow Qv and the leak flow Ql from the total flow Qt.

8.4.3.2 Therapy Engine Module 4320

In one form of the present technology, a therapy engine module 4320 may receive as inputs one or more of a pressure, Pm, in a patient interface 3000, and a respiratory flow of air to a patient, Qr, and provides as an output, one or more therapy parameters, such as a CPAP treatment pressure Pt, a level of pressure support, and a target ventilation.

In various forms of the present technology, the therapy engine module 4320 comprises one or more of the following algorithms: phase determination 4321, waveform determination 4322, ventilation determination 4323, flow limitation determination 4324, Apnea/hypopnea determination 4325, Snore determination 4326, Patency determination 4327 and Therapy parameter determination 4328.

A phase determination algorithm 4321 may receive as an input a signal indicative of respiratory flow, Qr, and provides as an output a phase of a breathing cycle of a patient 1000. The phase output may be a discrete variable with values of one of inhalation, mid-inspiratory pause, and exhalation. Alternatively the phase output is a continuous variable, for example varying from 0 to 1, or 0 to 2Pi.

In one form, the phase output is determined to have a discrete value of inhalation when a respiratory flow Qr has a positive value that exceeds a positive threshold. In one form, a phase is determined to have a discrete value of exhalation when a respiratory flow Qr has a negative value that is more negative than a negative threshold.

A waveform determination algorithm 4322 may receive as an input a value indicative of current patient ventilation, Vent, and provides as an output a waveform of pressure vs. phase. A ventilation determination algorithm 4323 may receive as an input a respiratory flow Qr, and determines a measure indicative of patient ventilation, Vent. For example the ventilation determination algorithm 4323 may determine a current value of patient ventilation, Vent, as half the low-pass filtered absolute value of respiratory flow, Qr.

A flow limitation determination algorithm 4324 may receive as an input a respiratory flow signal Qr and provides as an output a metric of the extent to which the inspiratory portion of the breath exhibits inspiratory flow limitation.

An Apnea/hypopnea determination algorithm 4325 may receive as an input a respiratory flow signal Qr and provide as an output a flag that indicates that an apnea or an hypopnea has been detected.

An apnea may be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

A hypopnea may be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

A snore determination algorithm 4326 may receive as an input a respiratory flow signal Qr and provides as an output a metric of the extent to which snoring is present. Preferably the snore determination algorithm 4326 comprises the step of determining the intensity of the flow signal in the range of 30-300 Hz. Further preferably, snore determination algorithm 4326 comprises a step of filtering the respiratory flow signal Qr to reduce background noise, e.g. the sound of airflow in the system from the blower. The snore determination algorithm 4326 may comprise comparing the noise generated during inspiration to the noise generated during expiration to determine the occurrence of snore, where the noise generated during expiration is considered to relate to the intrinsic device noise.

In one form an airway patency algorithm 4327 may receive as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In another form, an airway patency algorithm 4327 may receive as an input a respiratory flow signal Qr, and determines the presence or absence of a cardiogenic signal. The absence of a cardiogenic signal is taken to be an indication of a closed airway.

A therapy parameter determination algorithm 4328 determines a target treatment pressure Pt to be delivered by the PAP device 4000. The therapy parameter determination algorithm 4328 receives as an input one of more of the following:
  i. A measure of respiratory phase;
  ii. A waveform;
  iii. A measure of ventilation;
  iv. A measure of inspiratory flow limitation;
  v. A measure of the presence of apnea and/or hypopnea;
  vi. A measure of the presence of snore; and
  vii. A measure of the patency of the airway.

The therapy parameter determination algorithm 4328 determines the treatment pressure Pt as a function of indices or measures of one or more of flow limitation, apnea, hypopnea, patency, and snore. In one implementation, these measures are determined on a single breath basis, rather than on an aggregation of several previous breaths.

FIG. 5E is a flow chart illustrating a method 4500 carried out by the processor 4230 as one implementation of the algorithm 4328. The method 4500 starts at step 4520, at which the processor 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the processor 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the processor 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the processor 4230 increases the treatment pressure Pt by a predetermined pressure increment ΔP, provided the increased treatment pressure Pt would not exceed an upper limit Pmax. In one implementation, the predetermined pressure increment ΔP and upper limit Pmax are 1 $cmH_2O$ and 20 $cmH_2O$ respectively. The method 4500 then returns to step 4520.

At step 4560, the processor 4230 decreases the treatment pressure Pt by a decrement, provided the decreased treatment pressure Pt would not fall below a lower limit Pmin, such as a Pmin of 4 $cmH_2O$. The method 4500 then returns to step 4520. In one implementation, the decrement is proportional to the value of Pt-Pmin, so that the decrease in Pt to the lower limit Pmin in the absence of any detected events is exponential. Alternatively, the decrement in Pt could be predetermined, so the decrease in Pt to the lower limit Pmin in the absence of any detected events is linear.

8.4.3.3 Therapy Control Module 4330

A therapy control module 4330 in accordance with one aspect of the present technology may receive as an input a target treatment pressure Pt, and controls a therapy device 4245 to deliver that pressure. The therapy control module 4330 may receive as an input an EPAP pressure and an IPAP pressure, and controls a therapy device 4245 to deliver those respective pressures.

8.4.3.4 Detection of Fault Conditions

In one form of the present technology, a processor executes one or more methods for the detection of fault conditions serving as a fault condition module 4340. Preferably the fault conditions detected by the one or more methods includes at least one of the following:
  Power failure (no power, or insufficient power)
  Transducer fault detection
  Failure to detect the presence of a component
  Operating parameters outside recommended ranges (e.g. pressure, flow, temperature, $PaO_2$)
  Failure of a test alarm to generate a detectable alarm signal.

Upon detection of the fault condition, the corresponding algorithm signals the presence of the fault by one or more of the following:
  Initiation of an audible, visual &/or kinetic (e.g. vibrating) alarm
  Sending a message to an external device
  Logging of the incident 8.5 Humidifier 5000

8.5.1 Humidifier Overview

As shown in FIGS. 6A and 6B, a humidifier 5000 comprising a water reservoir 5110 and a heating plate 5120 may be provided and configured to couple directly or indirectly with a PAP device 4000. The water reservoir 5110 is configured to hold a supply of water 5300 that is heated by the heater plate 5120. The water reservoir 5110 may hold a given, maximum volume of liquid (e.g. water), typically several hundred millilitres. The water reservoir 5110 is arranged to receive a flow of breathable gas from the PAP device 4000 through an air inlet and to add humidity to the breathable gas. The humidified breathable gas exits the humidifier via an outlet for delivery to a patient interface (not shown) via an air delivery conduit 4170. The air delivery conduit may include a heated air delivery conduit 4172.

One or more transducers or sensors 5270, such as a temperature sensor, a relative humidity sensor, an absolute humidity sensor, a flow sensor or other such sensors may be present at one or more locations along the air path to measure the temperature, relative humidity, absolute humidity or flow rate at different locations to assist in controlling the humidifier and an optional heated air delivery conduit 4172. For example the heater plate 5120 may comprise a temperature sensor to measure the temperature of the heating plate. The one or more transducers or sensors 5270 may also be located external to the air path to measure the ambient conditions such as ambient temperature, ambient relative humidity and/or ambient absolute humidity.

A heated air delivery conduit 4172 may comprise a heating element 4173 within or around the heated air delivery conduit 4172. For example wires may be positioned between the film and supporting ribs of a heated tube. The heated air delivery conduit 4172 may also comprise one or more transducers or sensors 5270 as described above.

8.6 Glossary

For the purposes of the present technology disclosure, in certain forms of the present technology, one or more of the following definitions may apply. In other forms of the present technology, alternative definitions may apply.

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

Volute: The casing of the centrifugal pump that receives the air being pumped by the impeller, slowing down the flow rate of air and increasing the pressure. The cross-section of the volute increases in area towards the discharge port.

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:
  (i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20 \times 10^{-6}$ pascal (Pa), considered the threshold of human hearing.

8.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

Further example versions of the technology may be considered in the following descriptive paragraphs:

Example 1

A poly-phase switched reluctance motor assembly comprising:
a stator assembly including a plurality of coils and a stator with a central bore, and
a rotor assembly having a plurality of poles, the rotor assembly being arranged within the central bore of the stator assembly and configured to rotate therein,
wherein the plurality of coils are configured in a distributed winding configuration,
wherein the stator includes a plurality of projecting stator teeth forming a plurality of stator slots therebetween, and
wherein a total number of stator slots is a multiple of number of phases and number of rotor poles of the motor.

Example 2

The poly-phase switched reluctance motor assembly of Example 1 wherein each of the plurality of stator slots comprises a coil segment from one of the plurality of coils.

Example 3

The poly-phase switched reluctance motor assembly according to any one of Examples 1-2, wherein the total number of stator slots further comprises a multiple of a winding distribution parameter, such that the total number of stator slots satisfies an equation consisting of:

Total number of stator slots=number of phases×number of rotor poles×winding distribution parameter.

Example 4

The poly-phase switched reluctance motor assembly according to any one of Examples 1-3, wherein the plurality of coils includes a coil group for each phase of the poly-phase switched reluctance motor and each of the coils in a coil group includes a pair of coil segments, the coil segments for each coil group are uniformly distributed between the stator slots.

Example 5

The poly-phase switched reluctance motor assembly according to Example 4, wherein each coil group comprises at least one coil.

Example 6

The poly-phase switched reluctance motor assembly according to any one of Examples 1-5, including at least three motor phases and wherein in use two motor phases are energized and at least one phase is non-energized during a conduction period.

Example 7

The poly-phase switched reluctance motor assembly according to Example 6, wherein one of the two energized phases is switched off to a non-energized state and one of the non-energized phases is switched on to an energized state during each commutation period.

Example 8

The poly-phase switched reluctance motor assembly according to any one of Examples 6 or 7, wherein one of the two energized phases is provided with a positive direction current and the other of the two energized phases is provided with a negative direction current.

Example 9

The poly-phase switched reluctance motor assembly according to Example 8, wherein each phase of the motor is energized with a current value during at least two consecutive conduction periods.

Example 10

The poly-phase switched reluctance motor assembly according to any one of Examples 1-9, having an inductance ratio of less than 3.

Example 11

The poly-phase switched reluctance motor assembly according to Example 10, wherein the inductance ratio is between 2 and 2.5.

Example 12

The poly-phase switched reluctance motor assembly according to any one of Examples 1-11, wherein the stator has an outer diameter less than 50 mm.

Example 13

The poly-phase switched reluctance motor assembly according to Example 12, wherein the stator has an outer diameter less than or equal to 45 mm.

Example 14

The poly-phase switched reluctance motor assembly according to any one of Examples 1-13, wherein width of each rotor pole is wider than width of one of the plurality of stator teeth.

Example 15

The poly-phase switched reluctance motor assembly according to any one of Examples 1-14, wherein the distributed winding configuration comprises a plurality of phases with at least one phase of the plurality of phases comprising a plurality of coil winding groups.

Example 16

The poly-phase switched reluctance motor assembly according to any one of Examples 1-15 wherein each rotor pole width is equal.

Example 17

The poly-phase switched reluctance motor assembly according to any one of Examples 1-16 wherein each stator slot width is equal.

Example 18

The poly-phase switched reluctance motor assembly of any one of Examples 1-17 wherein the stator assembly and rotor assembly are configured to have a difference between a stator central angle and a rotor central angle in a difference range of 5 to 30 degrees.

Example 19

The poly-phase switched reluctance motor assembly of Example 18 wherein the difference between a stator central angle and a rotor central angle is about 27 degrees.

Example 20

The poly-phase switched reluctance motor assembly of any one of Examples 1-19 wherein each of the stator teeth comprises teeth tips.

Example 21

A stator assembly for a poly-phase switched reluctance motor comprising
a plurality of stator teeth separated by stator slots and surrounding a central bore,
a plurality of coils that are configured in a distributed winding configuration, the plurality of coils includes a coil group for each phase of the poly-phased switched reluctance motor,
wherein the central bore is configured to receive a rotor assembly having a plurality of poles and a total number of stator slots is a multiple of number of phases and number of rotor poles of the motor.

Example 22

The stator assembly according to Example 21, wherein each of the stator slots comprises a coil segment of one of the coils of the plurality of coils.

Example 23

The stator assembly according to any one of Examples 21-22, wherein each coil group comprises at least one coil.

Example 24

The stator assembly according to any one of Examples 21-23, wherein a width of each of the stator teeth of the plurality of stator teeth is less than a width of a rotor pole.

Example 25

The stator assembly according to any one of Examples 21-24, wherein the distributed winding configuration comprises a plurality of phases with at least one phase of the plurality of phases comprising a plurality of coil winding groups.

Example 26

The stator assembly according to any one of Examples 21-25 wherein rotor poles of the received rotor assembly have widths that are equal.

Example 27

The stator assembly according to any one of Examples 21-26 wherein each stator tooth width is equal.

Example 28

The stator assembly according to any one of Examples 21-27, wherein the total number of stator slots comprises a further multiple of a winding distribution parameter such that the total number of stator slots satisfies an equation consisting of:

Total number of stator slots=number of phases×number of rotor poles×winding distribution parameter.

Example 29

The stator assembly according to any one of Examples 21-28, wherein each of the coil segments for a coil group are uniformly distributed between the stator slots.

Example 30

The stator assembly according to any one of Examples 21-29, having an inductance ratio of less than 3.

Example 31

The stator assembly according to Example 30, wherein the inductance ratio is between 2 and 2.5.

Example 32

The stator assembly according to any one of Examples 21-31, wherein the stator has an outer diameter less than 50 mm.

Example 33

The stator assembly according to Example 32, wherein the stator has an outer diameter less than or equal to 45 mm.

Example 34

The stator assembly of any one of Examples 21-33 wherein the stator assembly and rotor assembly are configured to have a difference between a stator central angle and a rotor central angle in a difference range of 5 to 30 degrees.

Example 35

The stator assembly of Example 34 wherein the difference between the stator central angle and the rotor central angle is about 27 degrees.

Example 36

The stator assembly of any one of Examples 21-35 wherein each of the stator teeth comprises teeth tips.

Example 37

A positive airway pressure device comprising a poly-phase switched reluctance motor according to any one of Examples 1-20 configured to provide a supply of pressurized breathable gas.

Example 38

A system for treating a respiratory disorder comprising:
a therapy device comprising a poly-phase switched reluctance motor according to any one of Examples 1-20 configured to provide a supply of pressurized breathable gas;
an air delivery conduit; and
a patient interface configured to receive the supply of pressurized gas from the therapy device via the air delivery conduit and deliver the supply of pressurized gas to a patient.

Example 39

The system according to Example 38 further comprising a humidifier configured to humidify the supply of pressurized gas.

Example 40

A method of controlling a switched reluctance motor, the switched reluctance motor comprising at least three phases, the method comprising:
during each conduction period energizing a first phase with a negative direction current, energizing a second phase with a positive current and having at least one non-energized phase; and
during each commutation period switching off one of the first phase or the second phase to a non-energized state and switching on one of the non-energized phases to an energized state with a same direction current as the first or second phase that was switched off.

Example 41

The method according to Example 40, wherein the switched reluctance motor includes a distributed winding configuration.

Example 42

The method of any one of Examples 40-41 wherein the switched reluctance motor has a total number of stator slots that is a multiple of number of phases and number of rotor poles.

Example 43

The method of Example 42 wherein the total number of stator slots further comprises a multiple of a winding distribution parameter.

Example 44

The method of any one of Examples 40-43 wherein the switched reluctance motor has a stator assembly and rotor assembly configured to have a difference between a stator central angle and a rotor central angle in a difference range of 5 to 30 degrees.

Example 45

The method of Example 44 wherein the difference between the stator central angle and the rotor central angle is about 27 degrees.

Example 46

The method of any one of Examples 40-45 wherein the switched reluctance motor has a plurality of stator teeth, each comprising teeth tips.

Example 47

The method of any one of Examples 40-46 wherein the switched reluctance motor has only three phases.

Example 48

The method of any one of Examples 40-47 wherein the switched reluctance motor is a component of a therapy device configured to supply pressurized gas.

It is therefore to be understood that numerous modifications may be made to the illustrative embodiments and that other arrangements may be devised without departing from the spirit and scope of the technology.

The invention claimed is:

1. A method of controlling a switched reluctance motor, the switched reluctance motor comprising at least three phases, the method comprising:
during each conduction period energizing a first phase with a negative direction current, energizing a second phase with a positive direction current and having at least one non-energized phase; and
during each commutation period switching off one of the first phase or the second phase to a non-energized state and switching on one of the non-energized phases to an energized state with a same direction current as the first or second phase that was switched off,
wherein the switched reluctance motor uses a controller to apply direct current to two of the at least three phases.

2. The method according to claim 1, wherein the switched reluctance motor includes a distributed winding configuration.

3. The method of claim 1 wherein the switched reluctance motor has a total number of stator slots that is a multiple of number of phases and number of rotor poles.

4. The method of claim 3 wherein the total number of stator slots further comprises a multiple of a winding distribution parameter.

5. The method of claim 1 wherein the switched reluctance motor has a stator and rotor configured to have a difference between a stator central angle and a rotor central angle in a difference range of 5 to 30 degrees.

6. The method of claim 5 wherein the difference between the stator central angle and the rotor central angle is about 27 degrees.

7. The method of claim 1 wherein the switched reluctance motor has a plurality of stator teeth, each comprising teeth tips.

8. The method of claim 1 wherein the switched reluctance motor has only three phases.

9. The method of claim 1, wherein the controller detects and filters back electromotive force induced in the non-energized phase when a rotor of the switched reluctance motor rotates past the non-energized phase.

10. The method of claim 1, wherein further comprising energizing each phase of the switched reluctance motor with a current value during at least two consecutive conduction periods.

11. The method of claim 1 wherein the switched reluctance motor has an inductance ratio of less than 3.

12. The method of claim 1 wherein a stator of the switched reluctance motor has an outer diameter less than 50 mm.

13. The method of claim 1 wherein the switched reluctance motor has a rotor with a plurality of rotor poles and wherein each rotor pole has a width that is wider than a width of each of a plurality of stator teeth of a stator of the switched reluctance motor.

14. The method of claim 1 wherein operation of the switched reluctance motor rotates an impeller.

15. The method of claim 14 wherein rotation of the impeller produces a flow of air.

16. The method of claim 15 wherein the flow of air is produced with a volute of a blower.

17. The method of claim 16 wherein the flow of air supplies pressurized gas for a therapy.

* * * * *